(12) United States Patent
Pradeep et al.

(10) Patent No.: US 10,041,925 B2
(45) Date of Patent: Aug. 7, 2018

(54) DETECTION OF QUANTITY OF WATER FLOW USING QUANTUM CLUSTERS

(71) Applicant: Indian Institute of Technology, Chennai (IN)

(72) Inventors: Thalappil Pradeep, Chennai (IN); Leelavathi Annamalai, Kanjikoval (IN); Mohan Udhaya Sankar, Cuddalore (IN); Chaudhary Amrita, Varanasi (IN); Anshup, Lucknow (IN); Thumu Udayabhaskara Rao, West Godavari (IN)

(73) Assignee: Indian Institute of Technology, Chennai (IN)

( * ) Notice: Subject to any disclaimer, the term of this patent is extended or adjusted under 35 U.S.C. 154(b) by 0 days.

(21) Appl. No.: 14/394,825

(22) PCT Filed: Apr. 17, 2013

(86) PCT No.: PCT/IB2013/001244
§ 371 (c)(1),
(2) Date: Oct. 16, 2014

(87) PCT Pub. No.: WO2013/156870
PCT Pub. Date: Oct. 24, 2013

(65) Prior Publication Data
US 2015/0132856 A1    May 14, 2015

(30) Foreign Application Priority Data

Apr. 17, 2012  (IN) .......................... 1521/CHE/2012

(51) Int. Cl.
*G01N 33/20*   (2006.01)
*G01N 33/18*   (2006.01)
*G01N 21/78*   (2006.01)

(52) U.S. Cl.
CPC ......... *G01N 33/1893* (2013.01); *G01N 21/78* (2013.01)

(58) Field of Classification Search
None
See application file for complete search history.

(56) References Cited

U.S. PATENT DOCUMENTS 2,372,340 A    3/1945  Senyal
2,917,426 A    12/1959 Bugosh
(Continued)

FOREIGN PATENT DOCUMENTS

AE    1238/2012    6/2011
AE    219/2013     9/2011
(Continued)

OTHER PUBLICATIONS

Shen, Z. et al. Water-Soluble Fluorescent Ag Nanoclusters Obtained from Multiarm Star Poly(acrylic acid) as "Molecular Hydrogel", 2007, Advanced Materials, vol. 19, pp. 349-352.*
(Continued)

*Primary Examiner* — Xiaoyun R Xu
(74) *Attorney, Agent, or Firm* — Ballard Spahr LLP

(57) ABSTRACT

The preparation of silver quantum clusters embedded in organic-templated-boehmite-nanoarchitecture (OTBN) and its use as a sensor for quantity of water flow measured by change of color in visible light upon flow of contaminated water have been provided. Silver quantum clusters-embedded OTBN are highly luminescent. Since the quantum clusters are embedded in the matrix, they are highly stable over a long period of time. The composition described here is utilized in the form of a device for 'visible/ultraviolet light color change-based detection' upon passage of water through a water purification device. Upon interaction with ions present in water, luminescent silver clusters undergo (Continued)

chemical transformation to $Ag_2S$ nanoparticles. The transformation is reflected in the form of visible color change (from pink to black) and luminescence quenching (from red emission to negligible luminescence).

22 Claims, 10 Drawing Sheets

(56) References Cited

U.S. PATENT DOCUMENTS

| | | | |
|---|---|---|---|
| 3,013,901 | A | 12/1961 | Bugosh |
| 4,151,092 | A | 4/1979 | Grimm et al. |
| 4,250,058 | A | 2/1981 | Michalko |
| 4,684,471 | A | 8/1987 | Manojlovic |
| 4,769,143 | A | 9/1988 | Deutsch et al. |
| 4,918,426 | A | 4/1990 | Butts et al. |
| 5,051,189 | A | 9/1991 | Farrah |
| 5,064,534 | A | 11/1991 | Busch et al. |
| 5,288,399 | A | 2/1994 | Schulz |
| 5,458,766 | A | 10/1995 | Ehara et al. |
| 5,817,263 | A | 10/1998 | Taylor |
| 5,928,506 | A | 7/1999 | Bae |
| 5,981,052 | A | 11/1999 | Sugiyama |
| 5,990,373 | A | 11/1999 | Klabunde |
| 6,048,577 | A | 4/2000 | Garg |
| 6,054,056 | A | 4/2000 | Maziuk, Jr. et al. |
| 6,159,363 | A | 12/2000 | Collins et al. |
| 6,193,886 | B1 | 2/2001 | Nohren, Jr. |
| 6,319,487 | B1 | 11/2001 | Liu et al. |
| 6,585,885 | B2 | 7/2003 | Larkner et al. |
| 6,613,236 | B1 | 9/2003 | Guess et al. |
| 6,811,747 | B2 | 11/2004 | Silveri |
| 6,896,813 | B1 | 5/2005 | Harthill et al. |
| 6,908,551 | B2 | 6/2005 | King |
| 6,929,740 | B2 | 8/2005 | Hayes |
| 7,107,838 | B2 | 9/2006 | Chai et al. |
| 7,249,524 | B2 | 7/2007 | Williams et al. |
| 7,264,726 | B1 | 9/2007 | Levy |
| 7,309,429 | B2 | 12/2007 | Patil et al. |
| 7,329,301 | B2 | 2/2008 | Chang et al. |
| 7,396,461 | B2 | 7/2008 | Bommi et al. |
| 7,441,665 | B2 | 10/2008 | Bridges et al. |
| 7,449,030 | B2 | 11/2008 | Robson et al. |
| 7,585,409 | B2 | 9/2009 | Bommi et al. |
| 7,968,493 | B2 | 6/2011 | Sreekumaran Nair et al. |
| 8,932,983 | B1 | 1/2015 | Harris et al. |
| 2003/0019764 | A1 | 1/2003 | Baldwin et al. |
| 2003/0082133 | A1 | 5/2003 | Cooper et al. |
| 2003/0132172 | A1 | 7/2003 | Hayes |
| 2003/0148354 | A1 | 8/2003 | Gordon |
| 2003/0215513 | A1 | 11/2003 | Fyhr et al. |
| 2003/0232718 | A1 | 12/2003 | Cao et al. |
| 2004/0026657 | A1 | 2/2004 | Souter et al. |
| 2004/0048762 | A1 | 3/2004 | Stewart |
| 2004/0050795 | A1 | 3/2004 | Park et al. |
| 2004/0132607 | A1 | 7/2004 | Wood et al. |
| 2004/0149634 | A1 | 8/2004 | Hughes |
| 2004/0217326 | A1 | 11/2004 | Souter et al. |
| 2004/0267006 | A1 | 12/2004 | Yamane et al. |
| 2005/0003992 | A1 | 1/2005 | Del Duca et al. |
| 2005/0013759 | A1 | 1/2005 | Grow |
| 2005/0025970 | A1 | 2/2005 | Stipanovic |
| 2005/0040116 | A1 | 2/2005 | Purdy et al. |
| 2005/0072729 | A1 | 4/2005 | Bridges et al. |
| 2005/0092669 | A1 | 5/2005 | Ascher et al. |
| 2005/0154361 | A1 | 7/2005 | Sabesan |
| 2005/0193800 | A1 | 9/2005 | DeBoer et al. |
| 2005/0202244 | A1 | 9/2005 | Papagianakis |
| 2006/0000763 | A1 | 1/2006 | Rinker et al. |
| 2006/0144781 | A1 | 7/2006 | Carlson et al. |
| 2006/0254988 | A1 | 11/2006 | Frampton |
| 2006/0261000 | A1 | 11/2006 | Bassett et al. |
| 2007/0009809 | A1 | 1/2007 | Krekeler et al. |
| 2007/0042174 | A1 | 2/2007 | Rao et al. |
| 2007/0175196 | A1 | 8/2007 | Tepper et al. |
| 2007/0215536 | A1 | 9/2007 | Bommi et al. |
| 2007/0256981 | A1 | 11/2007 | Krogue et al. |
| 2008/0022940 | A1 | 1/2008 | Kirsch et al. |
| 2008/0023405 | A1 | 1/2008 | Rawson et al. |
| 2008/0053922 | A1 | 3/2008 | Honsinger et al. |
| 2008/0121584 | A1 | 5/2008 | Chen et al. |
| 2008/0202992 | A1 | 8/2008 | Bridges et al. |
| 2008/0210606 | A1 | 9/2008 | Burbank |
| 2008/0261321 | A1 | 10/2008 | Patton et al. |
| 2009/0001011 | A1 | 1/2009 | Knipmeyer et al. |
| 2009/0047311 | A1 | 2/2009 | Imahashi et al. |
| 2009/0081262 | A1 | 3/2009 | Toledano et al. |
| 2009/0111689 | A1 | 4/2009 | Burba, III |
| 2009/0142748 | A1 | 6/2009 | Smith et al. |
| 2009/0252709 | A1 | 10/2009 | Nose et al. |
| 2009/0264280 | A1 | 10/2009 | Lisetskiy et al. |
| 2009/0270253 | A1 | 10/2009 | Yang et al. |
| 2009/0291044 | A1 | 11/2009 | Seok et al. |
| 2010/0006508 | A1 | 1/2010 | Mitchell et al. |
| 2010/0044646 | A1 | 2/2010 | Zhamu et al. |
| 2010/0176037 | A1 | 7/2010 | Namespetra et al. |
| 2010/0209961 | A1 | 8/2010 | Kshirsagar et al. |
| 2010/0243572 | A1 | 9/2010 | Stouffer et al. |
| 2010/0272770 | A1 | 10/2010 | De Windt et al. |
| 2011/0094972 | A1 | 4/2011 | King et al. |
| 2011/0197657 | A1 | 8/2011 | Gole |
| 2011/0244012 | A1 | 10/2011 | Iida et al. |
| 2012/0125203 | A1 | 5/2012 | Fitzgerald et al. |
| 2012/0263777 | A1 | 10/2012 | Woo et al. |
| 2012/0330044 | A1 | 12/2012 | Hou |
| 2013/0168320 | A1 | 7/2013 | Pradeep et al. |
| 2013/0240439 | A1 | 9/2013 | Pradeep et al. |
| 2013/0292323 | A1 | 11/2013 | Pradeep et al. |
| 2014/0158625 | A1 | 6/2014 | Pradhan |
| 2014/0202943 | A1 | 7/2014 | Pradeep et al. |
| 2014/0216993 | A1 | 8/2014 | Pradeep et al. |
| 2014/0314951 | A1 | 10/2014 | Pradeep et al. |
| 2015/0132856 | A1 | 5/2015 | Pradeep et al. |
| 2016/0135468 | A1 | 5/2016 | Pradeep |

FOREIGN PATENT DOCUMENTS

| | | |
|---|---|---|
| AE | 325/2013 | 9/2011 |
| AE | 1012/2013 | 3/2012 |
| AE | 1080/2013 | 4/2012 |
| AE | 1161/2013 | 6/2012 |
| AE | PCT/IB2014/002316 | 6/2014 |
| AU | 2012241522 | 3/2012 |
| AU | 2012243079 | 4/2012 |
| AU | 2012251424 | 6/2012 |
| AU | 2012342118 | 11/2012 |
| AU | 2014338691 | 6/2014 |
| BH | 20120155 | 6/2011 |
| BH | 20130024 | 9/2011 |
| BH | 20130034 | 9/2011 |
| BH | 20130123 | 3/2012 |
| BH | 20130129 | 4/2012 |
| BH | PCT/IB2014/002316 | 6/2014 |
| BR | 112013024504 | 3/2012 |
| BR | 1120140125635 | 11/2012 |
| BR | 11 2015 032373 | 6/2014 |
| CA | 2270519 A1 | 11/2000 |
| CN | 1137490 A | 12/1996 |
| CN | 1113811 C | 7/2003 |
| CN | 1950301 A | 4/2007 |
| CN | 101218009 A | 7/2008 |
| CN | 101513188 A | 8/2009 |
| CN | 101628753 A | 1/2010 |
| CN | 101677575 A | 3/2010 |
| CN | 101700487 A | 5/2010 |
| CN | 102438719 A | 5/2012 |
| CN | 103179861 A | 6/2013 |
| CN | 103298550 A | 9/2013 |
| CN | 103339067 A | 10/2013 |
| CN | 103702730 A | 4/2014 |
| CN | 103747683 A | 4/2014 |
| CN | 103764245 A | 4/2014 |
| CN | PCT/IB2014/002316 | 6/2014 |

(56) References Cited

FOREIGN PATENT DOCUMENTS

| | | |
|---|---|---|
| CN | 104168996 A | 11/2014 |
| CN | 104520706 A | 4/2015 |
| EP | 0541231 B1 | 6/1996 |
| EP | 0938925 A1 | 9/1999 |
| EP | 1401573 A1 | 3/2004 |
| FR | 2905628 A1 | 3/2008 |
| GB | 1247572 A | 9/1971 |
| GB | 1269556 A | 4/1972 |
| GB | 2470382 A | 11/2010 |
| GC | 2012-22869 | 11/2012 |
| GC | 2013-23735 | 3/2013 |
| IL | 223388 | 6/2011 |
| IL | 224990 | 9/2011 |
| IL | 225524 | 9/2011 |
| IL | 228609 | 3/2012 |
| IL | 228824 | 4/2012 |
| IL | PCT/IB2012/001237 | 6/2012 |
| IL | PCT/IB2012/002885 | 11/2012 |
| IL | 235206 | 4/2013 |
| IL | PCT/IB2014/002316 | 6/2014 |
| IN | 200767 | 6/2006 |
| IN | 936/MUM/2008 | 11/2009 |
| IN | 1571/MUM/2008 | 1/2010 |
| IN | 169/CHE/2009 | 8/2010 |
| IN | 2893/CHE/2010 | 9/2010 |
| IN | 2089/CHE/2009 | 3/2011 |
| IN | 2433/CHE/2010 | 6/2012 |
| IN | 2563/CHE/2010 | 6/2012 |
| IN | 2892/CHE/2010 | 7/2012 |
| IN | 947/CHE/2011 | 10/2012 |
| IN | 1522/CHE/2011 | 11/2012 |
| IN | 4062/CHE/2011 | 6/2013 |
| IN | 4300/CHE/2011 | 6/2013 |
| IN | 2867/CHE/2013 | 2/2014 |
| IN | 9101/DELNP/2013 | 12/2014 |
| IN | 1529/CHE/2010 | 7/2015 |
| JP | 60-118285 | 6/1985 |
| JP | 62-192796 | 6/1989 |
| JP | 62-174909 | 7/1989 |
| JP | H04-225890 A | 8/1992 |
| JP | H06-306101 A | 11/1994 |
| JP | H08-141556 A | 6/1996 |
| JP | 10-180093 | 6/1998 |
| JP | 3049441 U | 6/1998 |
| JP | 11-189481 | 7/1999 |
| JP | H11-309368 A | 11/1999 |
| JP | 2004-305870 A | 11/2004 |
| JP | 2005-514510 A | 5/2005 |
| JP | 2006-068701 A | 3/2006 |
| JP | 2006-291031 A | 10/2006 |
| JP | 2008-030975 A | 2/2008 |
| JP | 2008-542001 A | 11/2008 |
| JP | 2010-129385 A | 6/2010 |
| JP | 2013-526567 | 9/2011 |
| JP | 2011-225521 A | 11/2011 |
| JP | 2013-505476 A | 2/2013 |
| JP | 2013-509551 A | 3/2013 |
| JP | 2015-506324 | 4/2013 |
| JP | 2013-527118 A | 6/2013 |
| JP | 2013-530908 | 8/2013 |
| JP | 2013-538686 A | 10/2013 |
| JP | 2014-509938 A | 4/2014 |
| JP | PCT/IB2014/002316 | 6/2014 |
| JP | 2014-516775 A | 7/2014 |
| JP | 2015-504364 A | 2/2015 |
| KR | 10-2013-7028290 | 3/2012 |
| KR | 2013-7031706 | 6/2012 |
| KR | 10-2014-7017385 | 11/2012 |
| KR | 1020167002153 | 6/2014 |
| MX | 2013011011 | 3/2012 |
| MX | 2013012788 | 6/2012 |
| MX | 2014012608 | 4/2013 |
| MX | 201507965 | 6/2014 |
| MX | 2013011745 A | 7/2014 |
| MX | 2014006245 A | 10/2014 |
| OM | PCT/IB2014/002316 | 6/2014 |
| PK | 7872012 | 11/2012 |
| QA | PCT/IB2014/002316 | 6/2014 |
| SA | PCT/IB2014/002316 | 6/2014 |
| SG | 201208847-2 | 6/2011 |
| SG | 10201504247 Y | 6/2011 |
| SG | 201301541-7 | 9/2011 |
| SG | 2013023544 | 9/2011 |
| SG | 201307205-3 | 3/2012 |
| SG | 201307554-4 | 4/2012 |
| SG | 11201402580 S | 11/2012 |
| SG | PCT/IB2014/002316 | 6/2014 |
| SG | 1120140258 S | 4/2015 |
| TW | 200516058 | 5/2005 |
| TW | 200833614 A | 8/2008 |
| WO | WO-97/41063 A1 | 11/1997 |
| WO | WO-02/064507 A2 | 8/2002 |
| WO | WO-03/000413 A1 | 1/2003 |
| WO | WO-03/043731 A1 | 5/2003 |
| WO | WO-2003/060003 A1 | 7/2003 |
| WO | WO-03/089112 A1 | 10/2003 |
| WO | WO-03/103800 A2 | 12/2003 |
| WO | WO-2004/000732 A1 | 12/2003 |
| WO | WO-2006/070953 A1 | 7/2006 |
| WO | WO-2006/072944 A2 | 7/2006 |
| WO | WO-2006/121932 A1 | 11/2006 |
| WO | WO-2006/0128187 A2 | 11/2006 |
| WO | WO-2007/010977 A1 | 1/2007 |
| WO | WO-2007/059832 A1 | 5/2007 |
| WO | WO-2007/117416 A2 | 10/2007 |
| WO | WO-2007/144256 A1 | 12/2007 |
| WO | WO-2008/020315 A2 | 2/2008 |
| WO | WO-2008/027530 A1 | 3/2008 |
| WO | WO-2008/106276 A2 | 9/2008 |
| WO | WO-2009/085553 A1 | 7/2009 |
| WO | WO-2009/150232 A2 | 12/2009 |
| WO | WO-2010/003267 A1 | 1/2010 |
| WO | WO-2010/022353 A1 | 2/2010 |
| WO | WO-2010/059165 A1 | 5/2010 |
| WO | WO-2010/096521 A2 | 8/2010 |
| WO | WO-2011/013142 A2 | 2/2011 |
| WO | WO-2011/015429 A2 | 2/2011 |
| WO | WO-2011/034544 | 3/2011 |
| WO | WO-2011/053158 | 5/2011 |
| WO | WO-2011/131722 A1 | 10/2011 |
| WO | WO-2011/141486 A1 | 11/2011 |
| WO | WO-2011/151725 A2 | 12/2011 |
| WO | WO-2012/028964 A2 | 3/2012 |
| WO | WO-2012/042388 A2 | 4/2012 |
| WO | WO-2012/140520 A2 | 10/2012 |
| WO | WO-2012/142025 A1 | 10/2012 |
| WO | WO-2012/150506 A2 | 11/2012 |
| WO | WO-2013/076581 A2 | 5/2013 |
| WO | WO-2013/156870 A2 | 10/2013 |
| WO | WO-2015/059562 A1 | 4/2015 |

OTHER PUBLICATIONS

Examination Report issued on Sep. 10, 2015 by Intellectual Property India for application 2893/CHE/2010, filed on Sep. 3, 2010 and published on Jul. 20, 2012 (Applicant—Indian Institute of Technology) (5 pages).

Adhikari, B. & A. Banerjee, Facile Synthesis of Water-Soluble Fluorescent Silver Nanoclusters and HgII Sensing, Chem Mater, 22(15):4364-71 (2010).

Ali et al., Advances in Water Treatment by Adsorption Technology, Nature Protocols, 1(6):2661 (2006).

Bandyopadhyaya et al., Silver-Embedded Granular Activated Carbon as an Antibacterial Medium for Water Purification, J Chem Technol Biotechnol, 83:1177-80 (2008).

Bhatnager, A. et al., Fluoride Removal from Water by Adsorption—A Review, Chemical Engineering Journal, 171:811-40 (2011).

Bootharaju, M.S. & T. Pradeep, Investigation into the Reactivity of Unsupported and Supported Ag7 and Ag8 Clusters with Toxic Metal Ions, Langmuir, 27(13):8134-43 (2011).

(56) References Cited

OTHER PUBLICATIONS

Brown et al., Observations on Halogens as Bathing Water Disinfectants, J Appl Microbiol, 29(3):559 (1966).

Chakraborty, I. et al., Luminescent Sub-Nanometer Clusters for Metal Ion Sensing: A New Direction in Nanosensors, J Haz Mater, 211-212:396-403 (2012).

Chandra et al., Water-Dispersible Magnetite-Reduced Graphene Oxide Composties for Arsenic Removal, ACS Nano, 4(7): 3979-3986 (2010).

Colwell et al., Reduction of Cholera in Bangledeshi Villages by Simple Filtration, PNAS, 100:1051-5 (2003).

Crittenden et al., Predicting GAC Performance with Rapid Small-Scale Column Tests, J Am Water Works Assoc, 83:77-87 (1991).

Dhanalakshmi, L. et al., Conversion of Double Layer Charge-Stabilized Ag©Citrate Colloids to Thiol Passivated Luminescent Quantum Clusters, Chem Commun, 48:859-61 (2012).

Diez, I. et al., Color Tunability and Electrochemiluminescence of Silver Nanoclusters, Angew Chem Ind Ed, 48(12):2122-5 (2009).

Dume, Belle, Graphene Soaks up Arsenic, Jul. 14, 2010, p. 1-2; Retrieved from http://web.archive.org/web/ 9 20100716215221/ http://environmentalresearchweb.org/cws/article/news/43168>.

Hijnen et al., Elimination of Viruses, Bacteria, and Protozoan Oocysts by Slow Sand Filtration, Water Sci Technol, 50(1):147-54 (2004).

Ho, Y.S. and G. McKay, The Kinetics of Sorption of Divalent Metal Ions onto Sphagnum Moss Peat Reaction Rate Models, Water Res, 34:735 (2000).

Hoek, E.M.V. et al., High-Throughput Screening of Silver Nanoparticle Stability and Bacterial Inactivation in Aquatic Media: Influence of Specific Ions, Environ Sci Technol, 44(19):7321-8 (2010).

Hu, Z. et al., Nanocomposite of Chitosan and Silver Oxide and Its Antibacterial Property, J Appl Polym Sci, 108(1): 52-6 (2008).

Hummers, W.S. and R.E. Offerman, Preparation of Graphitic Oxide, J Am Chem Soc, 80:1339 (1958).

Hurt, R.H., ed., International Committee for Characterization and Terminology of Carbon "First Publication of 30 Tentative Definitions," Journal of Carbon, 20(5):445-9 (1982).

Jagtap, S. et al., Synthesis and Characterization of Lanthanum Impregnated Chitosan Flakes for Fluoride Removal in Water, Destination, 273:267-75 (2011).

Jung et al., Antibacterial Activity and Mechanism of Action of the Silver Ion in *Staphylococcus aureus* and Escherichia coli, Appl Environ Microbol, 74(7):2171 (2008).

Kittler, S. et al., Toxicity of Silver Nanoparticles Increases During Storage Because of Slow Dissolution Under Release of Silver Ions, Chem Mater, 22(16):4548-54 (2010).

Koltuniewicz et al., Membranes in Clean Technologies: Theory and Practice, Wiley-VCH, vol. 1 (2008).

Kovtyukhova, N.I. et al., Layer-by-Layer Assembly of Ultrathin Composite Films from Micron-Sized Graphite Oxide Sheets and Polycations, Chem Mater, 11:771 (1999).

Lan, G.Y. et al., Silver Nanoclusters as Fluorescent Probes for Selective and Sensitive Detection of Copper Ions, Chem. Commun., 46:1257-9 (2010).

Ledo-Suárez, A. et al., Facile Synthesis of Stable Sub-Nanosized Silver Clusters in Microemulsions, Angew. Chem Int Ed, 46(46):8823-7 (2007).

Lee, T.H. et al., Single-Molecule Optoelectronics, Acc Chem Res, 38(7):534-41 (2005).

Leelavathi, A. et al., Supported Quantum Clusters of Silver as Enhanced Catalysts for Reduction, Nanoscale Res Lett, 6:123-32 (2011).

Li, D. et al., Processable Aqueous Dispersions of Graphene Nanosheets, Nat Nanotech, 3:101 (2008).

Liu, J. and R.H. Hurt, Ion Release Kinetics and Particle Persistence of Aqueous Nano-Silver Colloids, Environ Sci Technol, 44(6):2169-75 (2010).

Liu, R. et al., Defluoridation by Freshly Prepared Aluminum Hydroxide, 175:144-9 (2011).

Lixia, L.U. et al., Study on Preparation and Absorption of Fluorion of Chitosan Composite Microspheres, Chem Ind Times, 18(2):45-6 (2004).

Lopez-Lopez, M.T. et al., Stability and Magnetic Characterization of Oleate-Covered Magnetite Ferrofluids in Different Nonpolar Carriers, J Colloid Interface Sci, 291(1):144-51 (2005).

Makarava, N. et al., Water-Soluble Hybrid Nanoclusters with Extra Bright and Photostable Emissions: A New Tool for Biological Imaging, Biophys J, 89(1):572-80 (2005).

Mathew, A. et al., A Fifteen Atom Silver Cluster Confined in Bovine Serum Albumin, J Mater Chem, 21930):11205-12 (2011).

Miretzky, P. & A.F. Cirelli, Fluoride Removal from Water by Chitosan Derivatives and Composites: A Review, J Fluorine Chemistry, 132:231-40 (2011).

Mohapatra et al., Synthesis and Applications of Nano-Structured Iron Oxides/Hydroxides—A Review, International Journal of Engineering, Science and Technology, 2(8):127-46 (2010).

Mrudula, K.V. et al., Interfacial Synthesis of Luminescent 1 kDa Silver Clusters, J Mater Chem, 19(25):4335-42 (2009).

Muhammed, M.A.H. et al., Two Distinct Fluorescent Quantum Clusters of Gold Starting from Metallic Nanoparticles by pH-Dependent Ligand Etching, Nano Res, 1(4):333-40 (2008).

Muhammed, M.A.H., & T.Pradeep, Reactivity of Au25 Clusters with Au 3+, Chem Phys Lett, 449:186-190 (2007).

Oyanedel-Craver et al., Sustainable Collodial-Silver-Impregnated Ceramic Filter for Point-of-Use Water, Environ Sci Technol, 42:927-33 (2008).

Pal, S. et al., Does the Antibacterial Activity of Silver nanoparticles Depend on the Shape of the Nanoparticle? A Study of the Gram-Negative Bacterium *Escherichia coli*, Appl Environ Microbiol, 73(6):1712-20 (2007).

Patel, S.A. et al., Water-Soluble Ag Nanoclusters Exhibit Strong Two-Photon-Induced Fluoresence, J Am Chem Soc, 130(35):11602-3 (2008).

Peyser-Capadona, L. et al., Nanoparticle-Free Single Molecule Anti-Stokes Raman Spectroscopy, Phys Rev Lett, 94(5):058301 (2005).

Pradeep, T. et al., Noble Metal Nanoparticles for Water Purification: A Critical Review, Thin Solid Films, 517:6452 (2009).

Rao, T.U.B. & T. Pradeep, Luminescent Ag7 and Ag8 Clusters by Inerfacial Synthesis, Angew Chem Ind Ed, 49(23):3925-9 (2010).

Rao, T.U.B. et al., Ag7Au6: A 13-Atom Alloy Quantum Cluster, Angew Chem Ind Ed, 51(9):2155-9 (2012).

Rao, T.U.B. et al., Ag9 Quantum Cluster Through a Solid-State Route, J Am Chem Soc, 132(46):16304-7 (2010).

Shang, L. & S. Dong, Sensitive Detection of Cysteine Based on Fluorescent Silver Clusters, Biosens Bioelectron, 24(6):1569-73 (2009).

Sharma, J. et al., A Complementary Palette of Fluorescent Silver Nanoclusters, Chem Commun, 46(19):3280-2 (2010).

Shimizu, K. et al., Direct Dehydrogenative Amide Synthesis from Alcohols and Amines Catalyzed by ?-Alumina Supported Silver Cluster, Chem Eur J, 15(39):9977-80 (2009).

Shimizu, K. et al., Oxidant-Free Dehydrogenation of Alcohols Heterogeneously Catalyzed by Cooperation of Silver Clusters and Acid-Base Sites on Alumina, Chem Eur J, 15(10):2341-51 (2009).

Suidan et al., Reduction of Aqueous Free Chlorine with Granular Activated Carbon—pH and Temperature Effects, Environ Sci Technol, 11(8):785-9 (1977).

Sun, Y. et al., First Principles Studies of Two Luminescent Molecular Quantum Clusters of Silver, Ag7(H2MSA)7 and Ag8(H2MSA)8, Based on Experimental Fluorescence Spectra, J Phys Chem C, 115(42):20380-7 (2011).

Tiwari, Dhermendra K. et al., World Applied Science Journal, 3(3):417-33 (2008).

Vasireddy, D., Arsenic Adsorption onto Iron-Chitosan Composite from Drinking Water, Master os Science Thesis at Univ. of Missouri—Columbia (2005) (111 pages).

Vosch, T. et al., Strongly Emissive Individual DNA-Encapsulated Ag Nanoclusters as Single-Molecule Fluorophores, Proc Natl Acad Sci USA, 104(31):12616-21 (2007).

(56) References Cited

OTHER PUBLICATIONS

Warsakoon, E. et al., Defluorination of Drinking Water Using Layered Double Hydorxides, International Conference on Sustainable Built Environment, Kandy, 13-14, p. 64-6 (2010).
Xu, H. & K.S. Suslick, Sonochemical Synthesis of Highly Fluorescent Ag Nanoclusters, ACS Nano, 4(6):3209-14 (2010).
Xu, H. & K.S. Suslick, Water-Soluble Fluorescent Silver Nanoclusters, Adv Mater, 22(10):1078-82 (2010).
Zhang, H. and G. Chen, Potent Antibacterial Activities of $Ag/TiO_2$ Nanocomposite Powders Synthesized by a One-Pot Sol-Gel Method, Environ Sci Technol, 43(8):2905-10 (2009).
First Office Action issued on Nov. 24, 2014 by the State Intellectual Property Office of the People's Republic of China for Chinese Patent Application No. 2012800258421, which was filed on Apr. 10, 2012 and published as CN103764245 on Apr. 30, 2014 (Inventor—Pradhan et al.; Applicant—NanoHoldings, LLC) (10 pages).
Response to First Office Action filed on Jun. 29, 2015 with the State Intellectual Property Office of the People's Republic of China for Chinese Patent Application No. 2012800258421, which was filed on Apr. 10, 2012 and published as CN103764245 on Apr. 30, 2014 (Inventor—Pradhan et al.; Applicant—NanoHoldings, LLC) (4 pages).
International Search Report and Written Opinion mailed on Jul. 11, 2012 by the International Searching Authority for International Patent Application No. PCT/US2012/032880, which was filed on Apr. 10, 2012 and published as WO 2012/142025 on Oct. 18, 2012 (Inventor—Pradhan et al.; Applicant—NanoHoldings, LLC) (8 pages).
International Preliminary Report on Patentability issued on Oct. 15, 2013 by the International Searching Authority for International Patent Application No. PCT/US2012/032880, which was filed on Apr. 10, 2012 and published as WO 2012/142025 on Oct. 18, 2012 (Inventor—Pradhan et al.; Applicant—NanoHoldings, LLC) (6 pages).
Examination report issued on May 19, 2015 by the Intellectual Property Office of Singapore for Singaporean Patent Application No. 2013075544, which was filed on Apr. 10, 2012 (Inventor—Pradhan et al.;Applicant—NanoHoldings, LLC) (10 pages).
Search Report and Written Opinion issued Nov. 17, 2014 by the Intellectual Property Office of Singapore for Singaporean Patent Application No. 2013075544, which was filed on Apr. 10, 2012 (Inventor—Pradhan et al.; Applicant—NanoHoldings, LLC) (14 pages).
First Office Action issued on Dec. 3, 2013 by the State Intellectual Property Office of the People's Republic of China for Chinese Patent Application No. 201180037560.9, which was filed on Jun. 2, 2011 and published as CN103179861 on Jun. 26, 2013 (Inventor—Pradeep et al.; Applicant—NanoHoldings LLC) (7 pages).
Response to First Office Action filed on Jun. 18, 2014 by the State Intellectual Property Office of the People's Republic of China for Chinese Patent Application No. 201180037560.9, which was filed on Jun. 2, 2011 and published as CN103179861 on Jun. 26, 2013 (Inventor—Pradeep et al.; Applicant—NanoHoldings LLC) (15 pages).
Second Office Action issued Aug. 12, 2014 by the State Intellectual Property Office of the People's Republic of China for Chinese Patent Application No. 201180037560.9, which was filed on Jun. 2, 2011 and published as CN103179861 on Jun. 26, 2013 (Inventor—Pradeep et al.; Applicant—NanoHoldings LLC) (9 pages).
Response to Second Office Action filed on May 21, 2015 by the State Intellectual Property Office of the People's Republic of China for Chinese Patent Application No. 201180037560.9, which was filed on Jun. 2, 2011 and published as CN103179861 on Jun. 26, 2013 (Inventor—Pradeep et al.; Applicant—NanoHoldings LLC) (14 pages).
Examination Report issued on Feb. 24, 2015 by the Isreal Patent Office for Israeli Patent Application No. 223388, which was filed on Jun. 2, 2011 (Inventor—Pradeep et al; Applicant—NanoHoldings LLC) (3 pages).

International Search Report and Written Opinion mailed on Dec. 1, 2011 by the International Searching Authority for International Patent Application No. PCT/IB2011/001551, which was filed on Jun. 2, 2011 and published as WO 2011/151725 on Dec. 8, 2011 (Inventor—Pradeep et al.; Applicant—NanoHoldings LLC) (13 pages).
International Preliminary Report on Patentability issued on Dec. 4, 2012 by the International Searching Authority for International Patent Application No. PCT/IB2011/001551, which was filed on Jun. 2, 2011 and published as WO 2011/151725 on Dec. 8, 2011 (Inventor—Pradeep et al.; Applicant—NanoHoldings LLC) (12 pages).
Search Report and Written Opinion mailed on Mar. 11, 2014 by the Danish Patent and Trademark Office for Singaporean Patent Application No. 201208847-2, which was filed on Jun. 2, 2011 (Inventor—Pradeep et al.; Applicant—NanoHoldings LLC) (18 pages).
Preliminary Amendment filed on Dec. 3, 2012 with the U.S. Patent and Trademark Office for U.S. Appl. No. 13/701,561, filed Feb. 19, 2013 and published as US 2013/0168320 on Jul. 4, 2013 (Inventor—Pradeep et al.; Applicant—NanoHoldings LLC) (7 pages).
Restriction Requirement issued on Nov. 20, 2014 by the U.S. Patent and Trademark Office for U.S. Appl. No. 13/701,561, filed Feb. 19, 2013 and published as US 2013/0168320 on Jul. 4, 2013 (Inventor—Pradeep et al.; Applicant—NanoHoldings LLC) (8 pages).
Response to Restriction Requirement filed on May 20, 2015 with the U.S. Patent and Trademark Office for U.S. Appl. No. 13/701,561, filed Feb. 19, 2013 and published as US 2013/0168320 on Jul. 4, 2013 (Inventor—Pradeep et al.; Applicant—NanoHoldings LLC) (3 pages).
First Office Action issued Aug. 7, 2014 by the State Intellectual Property Office of the People's Republic of China for Chinese Patent Application No. 2011800529433, which was filed on Sep. 2, 2011 and published as CN103298550 on Sep. 11, 2013 (Inventor—Pradeep et al.; Applicant—NanoHoldings LLC) (7 pages).
Response to First Office Action filed on Jul. 20, 2015 with the State Intellectual Property Office of the People's Republic of China for Chinese Patent Application No. 2011800529433, which was filed on Sep. 2, 2011 and published as CN103298550 on Sep. 11, 2013 (Inventor—Pradeep et al.; Applicant—NanoHoldings LLC) (16 pages).
First Office Action issued on Apr. 20, 2015 by the Japan Patent Office for Japanese Patent Application No. 2013-526567, which was filed on Sep. 2, 2011 (Inventor—Pradeep et al.; Applicant—NanoHoldings LLC) (14 pages).
International Search Report and Written Opinion mailed on Apr. 23, 2013 by the International Searching Authority for International Patent Application No. PCT/IB2011/002740, which was filed on Sep. 2, 2011 and published as WO 2012/028964 on Mar. 8, 2012 (Inventor—Pradeep; Applicant—NanoHoldings, LLC) (7 pages).
International Preliminary Report on Patentability issued on May 21, 2013 by the International Searching Authority for International Patent Application No. PCT/IB2011/002710, which was filed on Sep. 2, 2011 and published as WO 2012/028964 on Mar. 8, 2012 (Inventor—Pradeep; Applicant—NanoHoldings, LLC) (6 pages).
Search Report and Written Opinion issued on May 27, 2014 by the Danish Patent and Trademark Office for Singaporean Patent Application No. 201301541-7, which was filed on Sep. 2, 2011 (Inventor—Pradeep et al.; Applicant—NanoHoldings LLC) (17 pages).
Preliminary Amendment filed on Mar. 1, 2013 with the U.S. Patent and Trademark Office for U.S. Appl. No. 13/820,403, filed May 14, 2013 and published as US 2013/0240439 on Sep. 19, 2013 (Inventor—Pradeep et al.; Applicant—NanoHoldings LLC) (6 pages).
First Office Action issued on Dec. 10, 2013 by the State Intellecutal Property Office of the People's Republic of China for Chinese Patent Application No. 2011800509092, which was filed on Sep. 30, 2011 and published as CN103339067 on Oct. 2, 2013 (Inventor—Pradeep et al.; Applicant—NanoHoldings LLC) (17 pages).
Response to First Office Action filed on Jun. 25, 2014 with the State Intellectual Property Office of the People's Republic of China for Chinese Patent Application No. 2011800509092, which was filed on Sep. 30, 2011 and published as CN103339067 on Oct. 2, 2013 (Inventor—Pradeep et al.; Applicant—NanoHoldings LLC) (14 pages).

(56) References Cited

OTHER PUBLICATIONS

Second Office Action issued on Jul. 15, 2014 by the State Intellectual Property Office of the People's Republic of China for Chinese Patent Application No. 2011800509092, which was filed on Sep. 30, 2011 and published as CN103339067 on Oct. 2, 2013 (Inventor—Pradeep et al.; Applicant—NanoHoldings LLC) (12 pages).
Response to Second Office Action filed on Nov. 28, 2014 with the State Intellectual Property Office of the People's Republic of China for Chinese Patent Application No. 2011800509092, which was filed on Sep. 30, 2011 and published as CN103339067 on Oct. 2, 2013 (Inventor—Pradeep et al.; Applicant—NanoHoldings LLC) (12 pages).
Third Office Action issued on Feb. 10, 2015 by the State Intellectual Property Office of the People's Republic of China for Chinese Patent Application No. 2011800509092, which was filed on Sep. 30, 2011 and published as CN103339067 on Oct. 2, 2013 (Inventor—Pradeep et al.; Applicant—NanoHoldings LLC) (11 pages).
Response to Third Office Action filed on Jun. 25, 2015 with the State Intellectual Property Office of the People's Republic of China for the Chinese Patent Application No. 2011800509092, which was filed on Sep. 30, 2011 and published as CN103339067 on Oct. 2, 2013 (Inventor—Pradeep et al.; Applicant—NanoHoldings LLC) (12 pages).
Office Action issued on Apr. 15, 2015 by the Japan Patent Office for Japanese Patent Application No. 2013-530819, which was filed on Sep. 30, 2011 and published as 2013-538686 on Oct. 17, 2013 (Inventor—Pradeep et al.; Applicant—NanoHoldings LLC) (10 pages).
International Search Report and Written Opinion mailed on May 15, 2012 by the International Searching Authority for International Patent Application No. PCT/IB2011/002790, which was filed on Sep. 30, 2011 and published as WO 2012/042388 on Apr. 5, 2012 (Inventor—Pradeep; Applicant—NanoHoldings, LLC) (8 pages).
International Preliminary Report on Patentability issued on Apr. 2, 2013 by the International Searching Authority for International Patent Application No. PCT/IB2011/002790, which was filed on Sep. 30, 2011 and published as WO 2012/042388 on Apr. 5, 2012 (Inventor—Pradeep; Applicant—NanoHoldings, LLC) (7 pages).
Search Report and Written Opinion issued on Mar. 3, 2015 by the Danish Patent and Trademark Office for Singaporean Patent Application No. 2013023544, which was filed on Sep. 30, 2011 (Inventor—Pradeep et al.; Applicant—NanoHoldings LLC) (13 pages).
Preliminary Amendment filed on Apr. 1, 2013 with the U.S. Patent and Trademark Office for U.S. Appl. No. 13/877,294, filed Jul. 11, 2013 and published as US 2013/0292323 on Nov. 7, 2013 (Inventor—Pradeep et al.; Applicant—NanoHoldings LLC) (7 pages).
Non-Final Office Action issued on Aug. 12, 2015 by the U.S. Patent and Trademark Office for U.S. Appl. No. 13/877,294, filed Jul. 11, 2013 and published as US 2013/0292323 on Nov. 7, 2013 (Inventor—Pradeep et al.; Applicant—NanoHoldings LLC) (17 pages).
First Office Action issued on Nov. 3, 2014 by the State Intellectual Property Office of the People's Republic of China for Chinese Patent Application No. 2012800219215, which was filed on Mar. 23, 2012 and published as CN103702730 on Apr. 2, 2014 (Inventor—Pradeep et al; Applicant—NanoHoldings LLC) (7 pages).
International Search Report and Written Opinion mailed on Dec. 6, 2012 by the International Searching Authority for Internationla Patent Application No. PCT/IB2012/001079, which was filed on Mar. 23, 2012 and published as WO 2012/140520 on Oct. 18, 2012 (Inventor—Pradeep et al.; Applicant—NanoHoldings LLC) (11 pages).
International Preliminary Report on Patentability issued on Oct. 1, 2013 by the International Searching Authority for International Patent Application No. PCT/IB2012/001079, which was filed on Mar. 23, 2012 and published as WO 2012/0140520 on Oct. 18, 2012 (Inventor—Pradeep et al.; Applicant—NanoHoldings LLC) (10 pages).

Search Report and Written Opinion issued on Apr. 7, 2015 by the Danish Patent and Trademark Office for Singaporean Patent Application No. 201307205-3, which was filed on Mar. 23, 2012 (Inventor—Pradeep et al; Applicant—NanoHoldings LLC) (21 pages).
Preliminary Amendment filed on Sep. 24, 2013 with the U.S. Patent and Trademark Office for U.S. Appl. No. 14/007,295, filed Mar. 27, 2014 and published as US 2014/0202943 on Jul. 24, 2014 (Inventor—Pradeep et al.; Applicant—NanoHoldings LLC) (3 pages).
First Office Action issued on Oct. 30, 2014 by the State Intellectual Property Office of the People's Republic of China for Chinese Patent Application No. 2012800247893, which was filed on Jun. 22, 2012 and published as CN103747683 on Apr. 23, 2014 (Inventor—Predeep et al; Applicant—NanoHoldings LLC) (8 pages).
Response to First Office Action filed on Aug. 6, 2015 with the State Intellectual Property Office of the People's Republic of China for Chinese Patent Application No. 2012800247893, which was filed on Jun. 22, 2012 and published as CN 103747683 on Apr. 23, 2014 (Inventor—Predeep et al; Applicant—NanoHoldings LLC) (10 pages).
Office Action issued on Jul. 21, 2015 by the Israel Patent Office for Israeli Patent Application No. PCT/IB2012/001237, which was filed on Jun. 22, 2012 (Inventor—Pradeep et al.; Applicant—NanoHoldings LLC) (2 pages).
International Search Report and Written Opinion mailed on Oct. 22, 2012 by the International Searching Authority for International Patent Application No. PCT/IB/2012/001237, which was filed on Jun. 22, 2012 and published as WO 2012/150506 on Nov. 8, 2012 (Inventor—Predeep et al.; Applicant—NanoHoldings LLC) (12 pages).
International Preliminary Report on Patentability issued on Nov. 5, 2013 by the International Searching Authority for International Patent Application No. PCT/IB/2012/001237, which was filed on Jun. 22, 2012 and published as WO 2012/150506 on Nov. 8, 2012 (Inventor—Predeep et al.; Applicant—NanoHoldings LLC) (10 pages).
Preliminary Amendment filed on Nov. 4, 2013 with the U.S. Patent and Trademark Office for U.S. Appl. No. 14/115,591, filed Dec. 2, 2013 and published US 2014/0216993 on Aug. 7, 2014 (Inventor—Pradeep et al.; Applicant—NanoHoldings LLC) (3 pages).
International Search Report and Written Opinion mailed Jun. 21, 2013 by the International Searching Authority for International Patent Application No. PCT/IB2012/002885, which was filed on Nov. 20, 2012 and published as WO 2013/076581 on May 30, 2013 (Inventor—Pradeep et al.; Applicant—NanoHoldings LLC) (8 pages).
International Preliminary Report on Patentability issued May 27, 2014 by the International Searching Authority for International Patent Application No. PCT/IB2012/002885, which was filed on Nov. 20, 2012 and published as WO 2013/076581 on May 30, 2013 (Inventor—Pradeep et al.; Applicant—NanoHoldings LLC) (7 pages).
Examination Report issued Mar. 10, 2015 by the Government of Pakistan Intellectual Property Organization—The Patent Office for Pakistani Patent No. 787/2012, which was filed on Nov. 22, 2012 (Inventor—Pradeep et al.; Applicant—NanoHoldings LLC) (2 pages).
Search Report issued Feb. 2, 2015 by the Intellectual Property Office of Singapore for Singaporean Patent No. 11201402580S, which was filed on Nov. 20, 2012 and granted as 11201402580S on Apr. 29, 2015 (Inventor—Pradeep et al.; Applicant—NanoHoldings LLC) (18 pages).
Notice of Grant issued Apr. 29, 2015 by the Intellectual Property Office of Singapore for Singaporean Patent No. 11201402580S, which was filed on Nov. 20, 2012 and granted as 11201402580S on Apr. 29, 2015 (Inventor—Pradeep et al.; Applicant—NanoHoldings LLC) (3 pages).
Preliminary Amendment filed on May 23, 2014 with the U.S. Patent and Trademark Office for U.S. Appl. No. 14/360,449, filed May 23, 2014 and published as US 2014/0314951 on Oct. 23, 2014 (Inventor—Pradeep et al.; Applicant—NanoHoldings LLC) (3 pages).
International Search Report and Written Opinion mailed Nov. 8, 2013 by the International Searching Authority for International Patent No. PCT/IB2013/001244, which was published on Apr. 17,

(56) References Cited

OTHER PUBLICATIONS 2013 and published as Wo 2013/156870 on Oct. 24, 2013 (Inventor—Pradeep et al.; Applicant—NanoHoldings LLC) (8 pages).
International Preliminary Report on Patentability issued Oct. 21, 2014 by the International Searching Authority for International Patent No. PCT/IB2013/001244, which was published on Apr. 17, 2013 and published as Wo 2013/156870 on Oct. 24, 2013 (Inventor—Pradeep et al.; Applicant—NanoHoldings LLC) (7 pages).
Preliminary Amendment filed on Oct. 16, 2014 with the U.S. Patent and Trademark Office for U.S. Appl. No. 14/394,825, filed Oct. 16, 2014 and published as US 2015/0132856 on May 14, 2015 (Inventor—Pradeep et al.; Applicant—NanoHoldings LLC) (3 pages).
International Search Report mailed on Mar. 13, 2015 by the International Searchnig Authority for International Patent Application No. PCT/IB2014/002316, which was filed on Jun. 27, 2014 and published as WO 2015/059562 on Apr. 30, 2015 (Inventor—Pradeep et al.; Applicant—NanoHoldings LLC) (3 pages).
First Office Action issued on Aug. 3, 3015 by the State Intellectual Property Office of the People's Republic of China for Chinese Patent Application No. 2012800612986 Inventor—Pradeep et al; Applicant—NanoHoldings LLC) (5 pages).
First Office Action issued on Aug. 21, 3015 by the State Intellectual Property Office of the People's Republic of China for Chinese Patent Application No. 201380025718X Inventor—Pradeep et al; Applicant—NanoHoldings LLC) (8 pages).
Non-Final Office Action issued on Sep. 24, 2015 by the U.S. Patent and Trademark Office for U.S. Appl. No. 13/820,403, filed May 14, 2014 (Inventor—Pradeep et al.; Applicant—NanoHoldings LLC) (15 pages).
Office Action issued on Sep. 25, 2015 by the Mexican Patent Office for application MX/a/2013/011745, filed on Oct. 9, 2013 (Applicant—Nanoholdings, Inc.) (4 pages).
Fourth Office Action issued on Oct. 23, 2015 by the State Intellecutal Property Office of the People's Republic of China for Chinese Patent Application No. 2011800509092, which was filed on Sep. 30, 2011 and published as CN103339067 on Oct. 7, 2013 (Inventor—Pradeep et al.; Applicant—NanoHoldings LLC) (12 pages).
Non-Final Office Action issued on Nov. 5, 2015 by the U.S. Patent and Trademark Office for U.S. Appl. No. 14/007,295, filed Mar. 27, 2014 (Inventor—Pradeep et al.; Applicant—NanoHoldings LLC) (21 pages).
Third Office Action issued on Dec. 11, 2015 by the State Intellectual Property Office of the People's Republic of China for Chinese Patent Application No. 2012800219215, which was filed on Mar. 23, 2012 and published as CN103702730 on Apr. 2, 2014 (Inventor—Pradeep et al; Applicant—NanoHoldings LLC) (6 pages).
Non-Final Office Action issued on Jul. 29, 2015 by the U.S. Patent and Trademark Office for U.S. Appl. No. 14/110,424, filed Feb. 21, 2014 and published as US 2014/0158625 on Jun. 12, 2014 (Inventor—Pradeep et al.; Applicant—NanoHoldings LLC) (7 pages).
Notice of Reasons for Rejection issued on Jan. 20, 2016 for application JP 2014-500489, filed on Mar. 25, 2011 (Applicant—NanoHoldings, LLC) (Original—3 pages // Translation—2 pages).
Notice of Reasons for Rejection issued on Mar. 8, 2016 for application JP 2013-530819, filed on Sep. 30, 2011 and published as JP 2013-538686 (Applicant—NanoHoldings, LLC) (Original—5 pages // Translation—5 pages).
Fourth Office Action issued on Mar. 2, 2016 by the State Intellectual Property Office of the People's Republic of China for Chinese Patent Application No. 201180037560.9, which was filed on Jun. 2, 2011 and published as CN103179861 on Jun. 26, 2013 (Inventor—Pradeep et al.; Applicant—NanoHoldings LLC) (Original 11 pages// Translation—9 pages).
Notice of Reasons for Rejection issued on Mar. 9, 2016 for application JP 2014-508886, filed on Jun. 22, 2012 and published as JP 2014516775 (Applicant—NanoHoldings LLC) (Original—5 pages // Translation—4 pages).
Final Office Action issued on Mar. 24, 2016 by the U.S. Patent and Trademark Office for U.S. Appl. No. 13/701,561, filed Feb. 19, 2013 and published as US 2013/0168320 on Jul. 4, 2013 (Inventor—Pradeep et al.; Applicant—NanoHoldings LLC) (51 pages).
Second Office Action was issued on Apr. 19, 2016 by the State Intellectual Property Office of the People's Republic of China for Chinese Application No. 2012800612986, filed on Nov. 20, 2012 and published as 104168996 on Nov. 26, 2014 (Inventor—Pradhan et al; Applicant—Indian Institute of Technology).
Third Office Action was issued on Apr. 25, 2016 by the State Intellectual Property Office of the People's Republic of China for Chinese Application No. 2012800258421, filed on Apr. 10, 2012 and published as CN103764245A on Apr. 30, 2014 (Inventor—Pradhan et al; Applicant—NanoHoldings, LLC) (Original—9 pages // Translated—15 pages).
Final Rejection was issued on May 27, 2016 by the U.S. Patent and Trademark Office for U.S. Appl. No. 14/110,424, filed Feb. 21, 2014 and published as US 2014-0158625 A1 on Jun. 21, 2014 (Inventor—Pradhan et al) (4 pages).
Final Rejection was issued on Jun. 10, 2016 by the U.S. Patent and Trademark Office for U.S. Appl. No. 13/877,294, filed Jul. 11, 2013 and published as US-2013-0292323-A1 on Nov. 7, 2013 (Inventor—Pradeep, et al) (15 pages).
Second Office Action was issued on Jun. 13, 2016 by the State Intellectual Property Office of the People's Republic of China for Chinese Application No. 201380025718X, filed on Apr. 17, 2013 and published as 104520706 on Apr. 15, 2015 (Inventor—Pradeep et al; Applicant—Indian Institute of Technology) (3 pages).
Final Rejection was issued on Jul. 14, 2016 by the U.S. Patent and Trademark Office for U.S. Appl. No. 14/007,295, filed Mar. 27, 2014 and published as US 2014-0202943 A1 on Jul. 24, 2014 (Inventor—Pradeep, et al) (21 pages).
Non-Final Rejection issued on Sep. 24, 2015 by the U.S. Patent and Trademark Office for U.S. Appl. No. 13/820,403, filed May 14, 2014 and published as US 2013-0240439 on Sep. 19, 2013 (Inventor—Pradeep, et al) (14 pages).
Response to Non-Final Rejection filed on Mar. 24, 2016 for U.S. Appl. No. 13/820,403, filed May 14, 2014 and published as US 2013-0240439 on Sep. 19, 2013 (Inventor—Pradeep, et al) (9 pages).
Final Rejection issued on Jul. 27, 2016 by the U.S. Patent and Trademark Office for U.S. Appl. No. 13/820,403, filed May 14, 2014 and published as US 2013-0240439 on Sep. 19, 2013 (Inventor—Pradeep, et al) (14 pages).
Patent Examination Report No. 1, issued on Jul. 21, 2106 by the IP Office of Australia for application 2012342118, filed on Nov. 20, 2012 (Inventor—Pradeep et al; Applicant—Indian Institute of Technology) (3 pages).
Examination Report issued by the GCC Patent Office on Mar. 21, 2016 for Application No. 2013-23735, filed on Mar. 3, 2013 (Inventor—Pradhan et al; Applicant—Indian Institute of Technology) (9 pages).
Final Office Action issued by the U.S. Patent and Trademark Office dated Sep. 13, 2016, for U.S. Appl. No. 14/115,591, filed Dec. 2, 2013 and published as U.S. 2014/0216993 dated Aug. 7, 2014 (Inventor—Pradeep et al.; Applicant—NanoHoldings LLC) (12 pages).
Notice of Reasons for Rejection dated Sep. 14, 2016, for application JP 2014-500489, filed on Mar. 25, 2011 (Applicant—NanoHoldings, LLC) (Original—2 pages // Translation—2 pages).
Fourth Office Action dated Oct. 21, 2016, by the State Intellectual Property Office of the People's Republic of China for Chinese Patent Application No. 2011800529433, which was filed on Sep. 2, 2011 and published as CN103298550 dated Sep. 11, 2013 (Inventor—Pradeep et al.; Applicant—NanoHoldings LLC) (Original—8 pages. // Translation—12 pages).
First Office Action dated Apr. 20, 2015 by the Japan Patent Office for Japanese Patent cc Application No. 2014-542953, which was filed on Nov. 20, 2012 (Inventor—Pradeep et al.; Applicant—NanoHoldings LLC) (6 pages).
Zhou, X. et al., In Situ Synthesis of Metal Nanoparticles on Single-Layer Graphene Oxide and Reduced Graphene Oxide Surfaces. J Phys Chem C. 2009; 113(25): 10842-6.

(56) References Cited

OTHER PUBLICATIONS

Zhu, W. et al., New, Safe, Efficient, Widely Applicable, Liquid Antibacterial Material of Silver Complex. Proceedings of the 8th China Antibacterial Industry Development Conference. 2012; pp. 213-5 (Abstract Only—1 page).
Fifth Office Action dated Jul. 12, 2017 by the SIPO for Patent Application No. 2011800529433, which was filed on Sep. 2, 2011 and published as CN 103298550 dated Sep. 11, 2013 (Inventor—Pradeep et al.) (Original—8 pages // Translation—8 pages).
Non-Final Office Action dated Feb. 15, 2017 by the U.S. Patent and Trademark Office for U.S. Appl. No. 14/360,449, filed May 23, 2014 and published as U.S. 2014/0314951 dated Oct. 23, 2014 (Inventor—Pradeep et al.; Applicant—Indian Institute of Technology) (16 pages).
Response to Non-Final Office Action filed Aug. 15, 2017 with the U.S. Patent and Trademark Office for U.S. Appl. No. 14/360,449, filed May 23, 2014 and published as U.S. 2014/0314951 dated Oct. 23, 2014 (Inventor—Pradeep et al.; Applicant—Indian Institute of Technology) (9 pages).
Certificate of Patent dated Mar. 1, 2017 by the SIPO for Patent Application No. 201380025718X, which was filed on Apr. 17, 2013 and granted as CN 104520706 dated Apr. 15, 2015 (Inventor—Pradeep et al.; Applicant—Indian Institute of Technology) (2 pages).
Notice of Reason for rejection dated May 1, 2017 by the Japanese Patent Office for Patent Application No. 2015-506324, which was filed on Apr. 17, 2013 and published as 2015-525337 dated Sep. 3, 2017 (Inventor—Pradeep et al.; Applicant—Indian Institute of Technology) (Original—2 pages // Translation—2 pages).
Examination Report No. 1 dated Jun. 7, 2016 by the Intellectual Property Office of Australia for Patent Application No. 2012243079, which was filed on Oct. 7, 2013 and granted dated Sep. 28, 2017 (Inventor—Pradhan et al.; Applicant—NanoHoldings, LLC) (3 pages).
Notice of Acceptance dated Jun. 6, 2017 by the Intellectual Property Office of Australia for Patent Application No. 2012243079, which was filed on Oct. 7, 2013 and granted dated Sep. 28, 2017 (Inventor—Pradhan et al.; Applicant—NanoHoldings, LLC) (3 pages).
Certificate of Patent dated Sep. 28, 2017 by the Intellectual Property Office of Australia for Patent Application No. 2012243079, which was filed on Oct. 7, 2013 and granted dated Sep. 28, 2017 (Inventor—Pradhan et al.; Applicant—NanoHoldings, LLC) (1 page).
Decision of Rejection dated Oct. 27, 2016 by the State Intellectual Property Office of the People's republic of China for Patent Application No. 2012800258421, which was filed on Nov. 27, 2013 and published as CN103764245 dated Apr. 30, 2014 (Inventor—Pradhan et al.; Applicant—NanoHoldings, LLC) (Original—10 pages; Translation—13 pages).
First Office Action dated Sep. 25, 2015 by the Mexican Patent Office for Patent Application No. MX/a/2013/011745, which was filed on Oct. 9, 2013 and granted as MX 347341 dated Apr. 21, 2017 (Inventor—Pradhan et al.; Applicant—NanoHoldings, LLC) (Original—3 pages; Translation—4 pages).
Second Office Action dated Mar. 22, 2016 by the Mexican Patent Office for Patent Application No. MX/a/2013/011745, which was filed on Oct. 9, 2013 and granted as MX 347341 dated Apr. 21, 2017 (Inventor—Pradhan et al.; Applicant—NanoHoldings, LLC) (Original—3 pages; Translation—3 pages).
Third Office Action dated Oct. 14, 2016 by the Mexican Patent Office for Patent Application No. MX/a/2013/011745, which was filed on Oct. 9, 2013 and granted as MX 347341 dated Apr. 21, 2017 (Inventor—Pradhan et al.; Applicant—NanoHoldings, LLC) (Original—3 pages; Translation—3 pages).
Certificate of Patent dated Apr. 21, 2017 by the Mexican Patent Office for Patent Application No. MX/a/2013/011745, which was filed on Oct. 9, 2013 and granted as MX 347341 dated Apr. 21, 2017 (Inventor—Pradhan et al.; Applicant—NanoHoldings, LLC) (1 page).
Notice of Appeal Filed filed Nov. 28, 2016 by the U.S. Patent and Trademark Office for U.S. Appl. No. 14/110,424, filed Feb. 21, 2014 and published as U.S. 2014/0158625 dated Jun. 12, 2014 (Inventor—Pradhan et al.; Applicant—NanoHoldings, LLC) (2 pages).
Notice of Abandonment dated Jul. 11, 2017 by the U.S. Patent and Trademark Office for U.S. Appl. No. 14/110,424, filed Feb. 21, 2014 and published as U.S. 2014/0158625 dated Jun. 12, 2014 (Inventor—Pradhan et al.; Applicant—NanoHoldings, LLC) (2 pages).
Decision of Rejection dated Oct. 17, 2016 by the State Intellectual Property Office of the People's republic of China for Patent Application No. 2012800258421, which was filed on Nov. 27, 2013 and published as CN103764245 dated Apr. 30, 2014 (Inventor—Pradhan et al.; Applicant—NanoHoldings, LLC) (Origina—12 pages; Translation—8 pages).
Office Action dated Sep. 8, 2015 by the Japanese Patent Office for Patent Application No. 2013-513004, which was filed on Dec. 3, 2012 and granted as JP 5908462 dated Apr. 1, 2016 (Inventor—Pradhan et al.; Applicant—NanoHoldings, LLC) (Translation Only—7 pages).
Certificate of Patent dated Apr. 1, 2016 by the Japanese Patent Office for Patent Application No. 2013-513004, which was filed on Dec. 3, 2012 and granted as JP 5908462 dated Apr. 1, 2016 (Inventor—Pradhan et al.; Applicant—NanoHoldings, LLC) (3 pages).
Notice of Appeal Filed filed Sep. 26, 2016 by the U.S. Patent and Trademark Office for U.S. Appl. No. 13/701,561, filed Feb. 19, 2013 and published as U.S. 2013/0168320 dated Jul. 4, 2013 (Inventor—Pradeep et al.; Applicant—NanoHoldings, LLC) (2 pages).
Notice of Abandonment dated May 5, 2017 by the U.S. Patent and Trademark Office for U.S. Appl. No. 13/701,561, filed Feb. 19, 2013 and published as U.S. 2013/0168320 dated Jul. 4, 2013 (Inventor—Pradeep et al.; Applicant—NanoHoldings, LLC) (2 pages).
Preliminary Amendment filed on Apr. 24, 2017 with the U.S. Patent and Trademark Office for U.S. Appl. No. 15/495,111, filed Apr. 24, 2017 (Inventor—Pradeep et al.; Applicant—NanoHoldings, LLC) (7 pages).
Notice of Abandonment dated Jan. 4, 2018 by the U.S. Patent and Trademark Office for U.S. Appl. No. 15/495,111, filed Apr. 24, 2017 (Inventor—Pradeep et al.; Applicant—NanoHoldings, LLC) (2 pages).
Office Action dated Mar. 8, 2016 by the Japanese Patent Office for Patent Application No. 2013-526567, which was filed on Sep. 2, 2011 (Inventor—Pradeep et al.; Applicant—NanoHoldings, LLC) (Translation Only—4 pages).
Final Rejection dated Oct. 5, 2016 by the Japanese Patent Office for Patent Application No. 2013-526567, which was filed on Sep. 2, 2011 (Inventor—Pradeep et al.; Applicant—NanoHoldings, LLC) (Translation Only—4 pages).
Notice of Appeal Filed filed Jan. 26, 2017 with the U.S. Patent and Trademark Office for U.S. Appl. No. 13/820,403, filed May 14, 2013 and published as U.S. 2013/0240439 dated Sep. 19, 2013 (Inventor—Pradeep et al.; Applicant—NanoHoldings, LLC) (2 pages).
Notice of Abandonment dated Oct. 6, 2017 by the U.S. Patent and Trademark Office for U.S. Appl. No. 13/820,403, filed May 14, 2013 and published as U.S. 2013/0240439 dated Sep. 19, 2013 (Inventor—Pradeep et al.; Applicant—NanoHoldings, LLC) (2 pages).
Preliminary Amendment filed on Aug. 25, 2017 with the U.S. Patent and Trademark Office for U.S. Appl. No. 15/686,294, filed Aug. 25, 2017 (Inventor—Pradeep et al.; Applicant—Indian Institute of Technology) (20 pages).
Decision of Rejection dated Jun. 7, 2016 by the State Intellectual Property Office of the People's Republic of China for Patent Application No. 2011800509092, which was filed on Sep. 30, 2011 and published as CN 103339067 dated Oct. 2, 2013 (Inventor—Pradeep et al.; Applicant—NanoHoldings, LLC) (Original—8 pages; Translation—2 pages).
Office Action dated Mar. 21, 2016 by the Israeli Patent Office for Patent Application No. 225524, which was filed on Sep. 30, 2011 (Inventor—Pradeep et al.; Applicant—NanoHoldings, LLC) (Original—2 pages; Translation—3 pages).
Final Rejection dated Aug. 29, 2016 by the Japanese Patent Office for Patent Application No. 2013-530819, which was filed on Sep. 30, 2011 and published as 2013-538686 dated Oct. 17, 2013

(56) References Cited

OTHER PUBLICATIONS (Inventor—Pradeep et al.; Applicant—NanoHoldings, LLC) (Original—3 pages; Translation—2 pages).
Notice of Appeal Filed filed Dec. 12, 2016 with the U.S. Patent and Trademark Office for U.S. Appl. No. 13/877,294, filed Jul. 11, 2013 and published as U.S. 2013/0292323 dated Nov. 7, 2013 (Inventor—Pradeep et al.; Applicant—NanoHoldings, LLC) (2 pages).
Notice of Abandonment dated Jul. 20, 2017 by the U.S. Patent and Trademark Office for U.S. Appl. No. 13/877,294, filed Jul. 11, 2013 and published as U.S. 2013/0292323 dated Nov. 7, 2013 (Inventor—Pradeep et al.; Applicant—NanoHoldings, LLC) (2 pages).
Examination Report No. 1 dated Jun. 1, 2016 by the Intellectual Property Office of Australia for Patent Application No. 2012241522, which was filed on Mar. 23, 2012 and granted on Sep. 21, 2017 (Inventor—Pradeep et al.; Applicant—Indian Institute of Technology) (3 pages).
Notice of Acceptance dated May 25, 2017 by the Intellectual Property Office of Australia for Patent Application No. 2012241522, which was filed on Mar. 23, 2012 and granted on Sep. 21, 2017 (Inventor—Pradeep et al.; Applicant—Indian Institute of Technology) (3 pages).
Certificate of Patent dated Sep. 21, 2017 by the Intellectual Property Office of Australia for Patent Application No. 2012241522, which was filed on Mar. 23, 2012 and granted on Sep. 21, 2017 (Inventor—Pradeep et al.; Applicant—Indian Institute of Technology) (1 page).
Certificate of Patent dated Nov. 23, 2016 by the State Intellectual Property Office of the People's Republic of China for Patent Application No. 201280021921.5, which was filed on Mar. 23, 2012 and granted as CN103702730 dated Nov. 23, 2016 (Inventor—Pradeep et al.; Applicant—Indian Institute of Technology) (1 page).
Certificate of Patent dated Aug. 10, 2017 by the Japanese Patent Office for Patent Application No. 2014-500489, which was filed on Mar. 23, 2012 and granted as 6188676 dated Aug. 10, 2017 (Inventor—Pradeep et al.; Applicant—Indian Institute of Technology) (1 page).
Examination Report dated Jul. 1, 2016 by the Intellectual Property Office of Singapore for Patent Application No. 20130702053, which was filed on Mar. 23, 2012 and granted as 193947 dated Oct. 4, 2016 (Inventor—Pradeep et al.; Applicant—Indian Institute of Technology) (13 pages).
Certificate of Grant dated Oct. 4, 2016 by the Intellectual Property Office of Singapore for Patent Application No. 20130702053, which was filed on Mar. 23, 2012 and granted as 193947 dated Oct. 4, 2016 (Inventor—Pradeep et al.; Applicant—Indian Institute of Technology) (1 page).
Notice of Appeal Filed filed Jan. 17, 2017 with the U.S. Patent and Trademark Office for U.S. Appl. No. 14/007,295, filed Mar. 27, 2014 and published as U.S. 2014/0202943 dated Jul. 24, 2014 (Inventor—Pradeep et al.; Applicant—Indian Institute of Technology) (2 pages).
Notice of Abandonment dated Aug. 23, 2017 by the U.S. Patent and Trademark Office for U.S. Appl. No. 14/007,295, filed Mar. 27, 2014 and published as U.S. 2014/0202943 dated Jul. 24, 2014 (Inventor—Pradeep et al.; Applicant—Indian Institute of Technology) (2 pages).
Preliminary Amendment filed on Aug. 15, 2017 with the U.S. Patent and Trademark Office for U.S. Appl. No. 15/677,618, filed Aug. 15, 2017 (Inventor—Pradeep et al.; Applicant—Indian Institute of Technology) (4 pages).
Second Office Action dated Sep. 17, 2015 by the State Intellectual Property Office of the People's Republic of China for Patent Application No. 201280024789.3, which was filed on Jun. 22, 2012 and granted as CN103747683 dated Feb. 15, 2017 (Inventor—Pradeep et al.; Applicant—Indian Institute of Technology) (Original—9 pages; Translation—10 pages).
Third Office Action dated Mar. 21, 2016 by the State Intellectual Property Office of the People's Republic of China for Patent Application No. 201280024789.3, which was filed on Jun. 22, 2012 and granted as CN103747683 dated Feb. 15, 2017 (Inventor—Pradeep et al.; Applicant—Indian Institute of Technology) (Original—4 pages; Translation—7 pages).
Certificate of Patent dated Feb. 14, 2017 by the State Intellectual Property Office of the People's Republic of China for Patent Application No. 201280024789.3, which was filed on Jun. 22, 2012 and granted as CN103747683 dated Feb. 15, 2017 (Inventor—Pradeep et al.; Applicant—Indian Institute of Technology) (1 page).
Second Examination Report dated Dec. 27, 2015 by the Israeli Patent Office for Patent Application No. 229223, which was filed on Jun. 22, 2012 and granted on Mar. 30, 2017 (Inventor—Pradeep et al.; Applicant—Indian Institute of Technology) (Translation Only—2 pages).
Certificate of Patent dated Mar. 30, 2017 by the Israeli Patent Office for Patent Application No. 229223, which was filed on Jun. 22, 2012 and granted on Mar. 30, 2017 (Inventor—Pradeep et al.; Applicant—Indian Institute of Technology) (1 page).
Notice of Appeal Filed filed Mar. 10, 2017 with the U.S. Patent and Trademark Office for U.S. Appl. No. 14/115,591, filed Dec. 2, 2013 and published as U.S. 2014/0216993 dated Aug. 7, 2014 (Inventor—Pradeep et al.; Applicant—Indian Institute of Technology) (2 pages).
Notice of Abandonment dated Nov. 22, 2017 by the U.S. Patent and Trademark Office for U.S. Appl. No. 14/115,591, filed Dec. 2, 2013 and published as U.S. 2014/0216993 dated Aug. 7, 2014 (Inventor—Pradeep et al.; Applicant—Indian Institute of Technology) (2 pages).
Preliminary Amendment filed on Oct. 10, 2017 with the U.S. Patent and Trademark Office for U.S. Appl. No. 15/728,561, filed Oct. 10, 2017 (Inventor—Pradeep et al.; Applicant—Indian Institute of Technology) (3 pages).
Notice of Acceptance dated Jul. 28, 2017 by the Intellectual Property Office of Australia for Patent Application No. 2012342118, which was filed on Nov. 20, 2012 (Inventor—Pradeep et al.; Applicant—Indian Institute of Technology) (3 pages).
Second Office Action dated Apr. 19, 2016 by the State Intellectual Property Office of the People's Republic of China for Patent Application No. 201280061298.6, which was filed on Nov. 20, 2012 and granted on Mar. 15, 2017 (Inventor—Pradeep et al.; Applicant—Indian Institute of Technology) (Original—3 pages; Translation—5 pages).
Certificate of Patent dated Mar. 15, 2017 by the State Intellectual Property Office of the People's Republic of China for Patent Application No. 201280061298.6, which was filed on Nov. 20, 2012 and granted on Mar. 15, 2017 (Inventor—Pradeep et al.; Applicant—Indian Institute of Technology) (1 page).
Second Examination Report dated Feb. 20, 2017 by the Patent Office of the Cooperation Council for the Arab States of the Gulf for Patent Application No. GC 2013-23735, which was filed on Mar. 3, 2013 (Inventor—Pradeep et al.; Applicant—Indian Institute of Technology) (Translation Only—4 pages).
Office Action dated Nov. 14, 2016 by the Japanese Patent Office for Patent Application No. 2014-542953, which was filed on Nov. 20, 2012 (Inventor—Pradeep et al.; Applicant—Indian Institute of Technology) (Translation Only—10 pages).
Notice of Allowance dated Nov. 27, 2017 by the U.S. Patent and Trademark Office for U.S. Appl. No. 14/360,449, filed May 23, 2014 and published as U.S. 2014/0314951 dated Oct. 23, 2014 (Inventor—Pradeep et al.; Applicant—Indian Institute of Technology) (8 pages).
Examination Report No. 1 dated Apr. 24, 2017 by the Intellectual Property Office of Australia for Patent Application No. 2014338691, which was filed on Jun. 27, 2014 (Inventor—Pradeep et al.; Applicant—Indian Institute of Technology) (4 pages).
Search Report dated Jun. 28, 2017 by the State Intellectual Property Office of the People's Republic of China for Patent Application No. 201480045660, which was filed on Jun. 27, 2014 (Inventor—Pradeep et al.; Applicant—Indian Institute of Technology) (2 pages).
First Office Action dated Jul. 3, 2017 by the State Intellectual Property Office of the People's Republic of China for Patent Application No. 201480045660, which was filed on Jun. 27, 2014 (Inventor—Pradeep et al.; Applicant—Indian Institute of Technology) (Original—4 pages; Translation—6 pages).

(56) References Cited

OTHER PUBLICATIONS

International Search Report and Written Opinion dated Mar. 13, 2015 by the International Searching Authority for Patent Application No. PCT/IB2014/002316, which was filed on Jun. 27, 2014 and published as WO 2015/059562 dated Apr. 30, 2015 (Inventor—Pradeep et al.; Applicant—Indian Institute of Technology) (8 pages).

International Preliminary Report on Patentability dated Dec. 29, 2015 by the International Searching Authority for Patent Application No. PCT/IB2014/002316, which was filed on Jun. 27, 2014 and published as WO 2015/059562 dated Apr. 30, 2015 (Inventor—Pradeep et al.; Applicant—Indian Institute of Technology) (6 pages).

Search Report dated Jun. 15, 2016 by the Intellectual Property Office of Singapore for Patent Application No. 11201510632W, which was filed on Jun. 27, 2014 (Inventor—Pradeep et al.; Applicant—Indian Institute of Technology) (3 pages).

Written Opinion dated Aug. 30, 2016 by the Intellectual Property Office of Singapore for Patent Application No. 11201510632W, which was filed on Jun. 27, 2014 (Inventor—Pradeep et al.; Applicant—Indian Institute of Technology) (7 pages).

Examination Report dated Apr. 10, 2017 by the Intellectual Property Office of Singapore for Patent Application No. 11201510632W, which was filed on Jun. 27, 2014 (Inventor—Pradeep et al.; Applicant—Indian Institute of Technology) (4 pages).

Certificate of Patent dated Nov. 28, 2017 by the Intellectual Property Office of Singapore for Patent Application No. 11201510632W, which was filed on Jun. 27, 2014 (Inventor—Pradeep et al.; Applicant—Indian Institute of Technology) (1 page).

Preliminary Amendment filed on Dec. 22, 2015 with the U.S. Patent and Trademark Office for U.S. Appl. No. 14/900,740, filed Dec. 22, 2015 and published as U.S. 2016/0135468 dated May 19, 2016 (Inventor—Pradeep et al.; Applicant—Indian Institute of Technology) (6 pages).

Examination Report and Search Report dated Mar. 12, 2018 by the United Arab Emirates Ministry of Economy for Patent Application No. 1161/2013, which was filed on Oct. 31, 2013 (Inventor—Pradeep et al.; Applicant—Indian Institute of Technology) (11 pages).

Notice of Allowance dated Apr. 5, 2018 by the U.S. Patent and trademark Office for U.S. Appl. No. 14/360,449, filed May 23, 2014 and published as U.S. 2014/0314951 dated Oct. 23, 2014 (Inventor—Pradeep et al.; Applicant—Indian Institute of Technology) (5 pages).

Office Action dated Apr. 9, 2018 by the Japanese Patent Office for Patent Application No. 2016-522896, which was filed on Feb. 25, 2016 and published as 2016-523284 dated Aug. 8, 2016 (Inventor—Pradeep et al.; Applicant—Indian Institute of Technology) (Original—6 pages; Translation—9 pages).

Restriction Requirement dated Mar. 16, 2018 by the U.S. Patent and Trademark Office for U.S. Appl. No. 14/900,740, filed Dec. 22, 2015 and published as U.S. 2016/0135468 dated May 19, 2016 (Inventor—Pradeep et al.; Applicant—Indian Institute of Technology) (10 pages).

Response to Restriction Requirement filed on May 16, 2018 with the U.S. Patent and Trademark Office for U.S. Appl. No. 14/900,740, filed Dec. 22, 2015 and published as U.S. 2016/0135468 dated May 19, 2016 (Inventor—Pradeep et al.; Applicant—Indian Institute of Technology) (3 pages).

Non-Final Office Action dated May 31, 2018 by the U.S. Patent and Trademark Office for U.S. Appl. No. 14/900,740, filed Dec. 22, 2015 and published as U.S. 2016/0135468 dated May 19, 2016 (Inventor—Pradeep et al.; Applicant—Indian Institute of Technology) (13 pages).

\* cited by examiner

DETECTION OF QUANTITY OF WATER FLOW USING QUANTUM CLUSTERS

CROSS-REFERENCE TO RELATED APPLICATIONS

The present application is a U.S. National Phase Application of International Application No. PCT/IB2013/001244, filed Apr. 17, 2013, which claims priority to Indian Patent Application No. 1521/CHE/2012, filed Apr. 17, 2012, both of which applications are incorporated herein fully by this reference.

BACKGROUND

Technical Field

The present disclosure relates to the preparation of silver quantum cluster embedded in organic-templated-boehmite-nanoarchitecture (OTBN) and its use as a color changing sensor in the visible light or UV light for assessing the quantity of water passed through a water purification device.

Technical Background

The objective of providing safe and affordable drinking water is a global mission and it is eloquently articulated in United Nations Millennium Development Goal 2015, United Nations General Assembly resolutions (64/292 and 65/154) and article 47 of Indian Constitution. A major contribution to this can be made by providing an affordable safe drinking water at point-of-use, which is so far restricted largely due to un-availability of eco-conscious technology.

For the past several years, various research groups are working on developing novel materials for water purification. An affordable and all-inclusive water purifier which removes broad range of contaminants such as pesticides has been disclosed by Indian patent 200767 and U.S. Pat. No. 7,968,493, for removing microorganisms has been disclosed by Indian patent 20070608 and Indian patent applications 947/CHE/2011 and 4300/CHE/2011, for removing fluorides has been disclosed by Indian patent applications 2089/CHE/2009, 1529/CHE/2010 and 4062/CHE/2011, and for removing heavy metals has been disclosed by Indian patent applications 169/CHE/2009, 2433/CHE/2010 and 2563/CHE/2010. The water purification device is further described in Indian patent applications 2892/CHE/2010 and 1522/CHE/2011.

An important aspect of a water purifier is to ensure delivery of quality output water throughout the stated life of the purifier. Usually it is quite difficult for a consumer to keep a note of volume of water passed through a water purifier. Unlike other consumer goods such as refrigerator, washing machine, etc., water purifier may still continue to function even though its performance may have shrunk significantly. The quality of output water directly relates to the health of consumer. Hence, it is necessary to ensure a reasonable check on the output water quality.

As it would be evident from prior art that such a check on the output water quality is typically enforced using a flow meter which measures the volume of water passed. Owing to lack of actual water quality measurement at field, it is a first line of defense for output water quality. However, as it is well known that water quality across India varies significantly due to which the performance of water purification device also varies. Hence, it is important to have a second line of defense as simultaneous measurement of volume of water passed along with the input water quality. Depending on the input water quality, the measurement of volume of water should indicate if the water purification device is exhausted. This is an important premise of the invention articulated in this application.

Quantum clusters of noble metals are a class of new materials which are less than 1 nm in core dimension, nearly equal to Fermi wavelength of an electron (~0.5 nm for silver, M. A. H. Muhammed, T. Pradeep, in Advanced fluorescence reporters in chemistry and biology II: Molecular constructions, polymers and nanoparticles, Alexander P. Demchenko (ed.), 2010, Springer, Heidelberg). These are distinctly different from nanoparticles. In them band structure breaks into discrete energy levels, they have very high confinement in electronic structure, they exhibit molecular properties such as luminescence and plasmon resonance usually found with nanoparticles is absent. Due to these properties, quantum clusters have new utility in several applications such as optical storage, biological labels, catalysis, sensors, magnetism, optical absorption tunability, etc.

Sensitivity of clusters to metal ions were reported by the group (Reactivity of $Au_{25}$ clusters with $Au^{3+}$, M. A. Habeeb Muhammed, T. Pradeep, Chem. Phys. Lett., 2007, 449, 186-190). Fluorescent clusters are used as sensitive and easy probes for heavy metal ions in environmental samples such as pond water and soil by fluorescent turn-on mechanism (G.-Y. Lan, C.-C. Huang, H.-T. Chang, Chem. Commun., 2010, 46, 1257-1259). A new class of water soluble silver clusters with high two-photon excitation cross-section providing tunability in excitation and emission wavelengths can be used as highly sensitive biolabels (S. A. Patel, C. I. Richards, J.-C. Hsiang, R. M. Dickson, J. Am. Chem. Soc, 2008, 130, 11602-11603). DNA sequences templated silver clusters have been synthesized which can be tuned for fluorescence emission wavelength by varying the DNA template, implying useful biological applications (J. Sharma, H.-C. Yeh, H. Yoo, James H. Werner, J. S. Martinez, Chem. Commun., 2010, 46, 3280-3282). Properties of water soluble fluorescent silver clusters can be varied by adopting different synthetic routes and their stabilizing polymer ligand (H. Xu, K. S. Suslick, Adv. Mater., 2010, 22, 1078-1082). Water-soluble Ag-thioflavin T nanoclusters has been demonstrated for use in tracking of ultrasensitive biological assays both in vitro and in vivo (N. Makarava, A. Parfenov, I. V. Baskakov, Biophys. J., 2005, 89, 572-580). An important biological analyte, cysteine can be sensed at low concentration by poly(methacrylic acid) templated silver clusters with specific fluorescent quenching mechanism (L. Shang, S. Dong, Biosens. Bioelectron, 2009, 24, 1569-1573). Quantum optoelectronic logic operations can be created with electroluminescence of individual silver nanoclusters at room temperature (T.-H. Lee, J. I. Gonzalez, J. Zheng, R. M. Dickson, Acc. Chem. Res., 2005, 38, 534-541). DNA-encapsulated Ag nanoclusters exhibit high fluorescence in the near IR, enabling a single-molecule-specific bunching feature (T. Vosch, Y. Antoku, J.-C. Hsiang, C. I. Richards, J. I. Gonzalez, R. M. Dickson, PNAS, 2007, 104, 12616-12621). Metal oxide supported silver quantum clusters are used as a catalyst (A. Leelavathi, T. U. B. Rao, T. Pradeep, Nanoscale Res. Lett, 2011, 6, 123-132). Dehydrogenation of alcohols to carbonyl compounds by supported silver clusters has also been reported (K. Shimizu, K. Sugino, K. Sawabe, A. Satsuma, Chem. Eur. J. 2009, 15, 2341-2351). Alumina supported silver clusters have been used for direct amide synthesis from alcohols and amines with high selectivity (K. Shimizu, K. Ohshima, A. Satsuma, Chem. Eur. J. 2009, 15, 9977-9980). Poly(methacrylic acid) stabilized silver nanoclusters respond to the environment by having solvatochromic and solvato-fluorochromic (i.e., absorption and emission properties) responses useful for molecular sensing (I. Diez, M. Pusa, S. Kulmala, H. Jiang, A. Walther, A. S. Goldmann, A. H. E. Müller, O. Ikkala, R. H. A. Ras, Angew. Chem. Int. Ed. 2009, 48, 2122-2125).

Poly(methacrylic acid) stabilized silver nanoclusters prepared by sonochemical method can be used for bioimaging, chemical and biosensing, single-molecule studies, and possibly catalysis (H. Xu, K. S. Suslick, ACS Nano, 2010, 4, 3209-3214). Sub-nanometer clusters are used as Raman labels to identify true chemical information about single molecules (L. P.-Capadona, J. Zheng, J. I. Gonzalez, T.-H. Lee, S. A. Patel, R. M. Dickson, Phys. Rev. Lett., 2005, 94, 058301). Silver clusters synthesized by micro-emulsion method display paramagnetic behavior (A. L.-Suarez, J. Rivas, C. F. R.-Abreu, M. J. Rodriguez, E. Pastor, A. H.-Creus, S. B. Oseroff, M. A. L.-Quintela, Angew. Chem. Int. Ed., 2007, 46, 8823-8827). Water soluble fluorescent sliver clusters have also been used for metal ion sensing (K. V. Mrudula, T. U. B. Rao, T. Pradeep, J. Mater. Chem., 2009, 19, 4335-4342; B. Adhikari, A. Banerjee, Chem. Mater., 2010, 22, 4365).

Silver quantum clusters have also been studied from various perspectives: synthesis (various kinds of molecular clusters), characterization and utility (sensing and catalysis). Several other applications such as metal ion sensing and cell imaging were done with gold clusters as well. A representative list for silver clusters is given as follows:

Synthesis (i) $Ag_7Au_6$: A 13 atom alloy quantum cluster, T. U. B. Rao, Y. Sun, N. Goswami, S. K. Pal, K. Balasubramanian, T. Pradeep, Angew. Chem. Int. Ed., 2012, 51, 2155-2159
(ii) Conversion of double layer charge-stabilized Ag@citrate colloids to thiol passivated luminescent quantum clusters, L. Dhanalakshmi, T. U. B. Rao, T. Pradeep, Chem. Commun., 2012, 48, 859-861
(iii) A fifteen atom silver cluster confined in bovine serum albumin, A. Mathew, P. R. Sajanlal, T. Pradeep, J. Mater. Chem., 2011, 21, 11205-11212
(iv) $Ag_9$ quantum cluster through a solid state route, T. U. B. Rao, B. Nataraju, T. Pradeep, J. Am. Chem. Soc., 2010, 132, 16304-16307
(v) Luminescent $Ag_7$ and $Ag_8$ Clusters by interfacial synthesis, T. U. B. Rao, T. Pradeep, Angew. Chem. Int. Ed., 2010, 49, 3925-3929

Characterization (i) First principle studies of two luminescent molecular quantum clusters of silver, $Ag_7(H_2MSA)_7$ and $Ag_8$ $(H_2MSA)_8$ based on experimental fluorescence spectra, Y. Sun, K. Balasubramanian, T. U. B. Rao, T. Pradeep, J. Phys. Chem. C, 2011, 115, 42, 20380-20387

Utility (i) Supported quantum clusters of silver as enhanced catalysts for reduction, A. Leelavathi, T. U. B. Rao, T. Pradeep, Nanoscale Research Letters, 2011, 6, 123-132
(ii) Investigation into the reactivity of unsupported and supported $Ag_7$ and $Ag_8$ clusters with toxic metal ions, M. S. Bootharaju, T. Pradeep, Langmuir, 2011, 27, 8134-8143
(iii) Luminescent sub-nanometer clusters for metal ion sensing: a new direction in nanosensors, I. Chakraborty, T. U. B. Rao, T. Pradeep, J. Haz. Mater., 2012, 211-212, 396-403

An important objective of providing clean and affordable drinking water to masses is to ensure delivery of pure water at the point-of-use. Ensuring the consumption of clean drinking water would facilitate realization of the fundamental right to life, of which clean water is a recognized component. This is also an important component of the United Nations Millennium Development Goal 2015.

In order to ensure quality drinking water at point-of-use, there are two possible approaches technologically. First is to develop an affordable sensor for detection of trace concentrations of drinking water contaminants, especially microorganisms. This approach is still under development at various research laboratories across the world. Second is to integrate a flow meter with a rigorously tested water purifier having a known life. Flow meter will tell the user when the known life of the water purifier is over and consumables such as the cartridge require a change. Indeed, the first approach is more reliable; however, since the technologies are still under development, it is wise to look at flow meters till a reliable solution is ready.

It is also to be noted that gravity-fed storage water purifiers can't operate with typical flow meters due to unavailability of high pressures (P<0.5 psi). In such cases, a few approaches have been reported for the detection of volume of water passed.

Ahmad et al. in WO 2011/013142 have reported the use of a mechanical device along with a tablet made of sparingly water soluble salts. Intent is to have the tablet slowly dissolve upon passage of pre-determined volume of water. Once the tablet is dissolved, a mechanical action is initiated which blocks the flow of the liquid.

Another attempt is reported by Jambekar et al. in WO 2007/144256, wherein the biocide used is sparingly soluble in water and upon its dissolution, a mechanical action initiates the closure of water flow.

Ehara et al. in U.S. Pat. No. 5,458,766 have utilized battery along with a LED for determination of lifetime of the filter. Williams et al. in U.S. Pat. No. 7,249,524 have used an impeller device as a sensor for determining the flow and volume of water passing through the cartridge. Larkner et al. in U.S. Pat. No. 6,585,885 have reported a water purification system containing a sensing element coupled with an electronic control for accurately indicating the volume of water. Butts et al. in U.S. Pat. No. 4,918,426 have reported an in-line filter consisting of a flow meter with no moving parts to measure the total volume of the fluid filtered. Chai et al. in U.S. Pat. No. 7,107,838 have reported a water filter consisting of an electrode pair for sensing volume of the water dispensed. Guess et al. in U.S. Pat. No. 6,613,236 have used a tri-color LED emission for indicating volume of the water passed through the filter.

This invention reports the detection of volume of water passed through a water purification device, by use of a novel composition which undergoes change in the color upon continuous interaction with salts usually found in drinking water. The aspect of color change in nanomaterial, especially noble metal nanoparticles, upon interaction with ionic salts is well-studied. The conclusion from prior art is that nanoparticles undergo instant aggregation upon exposure to mild concentration of salts. This is due to the reduction in surface energy of metal nanoparticles upon interaction with the counter ion. Usually, the aggregation of metal nanoparticles, especially silver, is almost instantaneous at salt concentrations of 100 ppm and above.

In light of the foregoing discussion, there exists a need to address the aforementioned problems and other shortcomings associated with the prior art methods and compositions. These needs and other needs are satisfied by the method and device described in the present disclosure.

SUMMARY

In accordance with the purpose(s) of the invention, as embodied and broadly described herein, this disclosure, in one aspect, relates to water purification. Particularly the disclosure relates to the preparation of silver quantum cluster embedded in organic-templated-boehmite-nanoarchitecture (OTBN) and its use as a color changing sensor in the visible light or UV light for assessing the quantity of water passed through a water purification device.

An object of the present invention is to synthesize silver clusters in the OTBN matrix for protecting the silver quantum clusters from the segregation of common ions present in the drinking water.

Another object of the present invention is to provide a method for preparing a silver quantum clusters embedded in organic-templated-boehmite-nanoarchitecture (OTBN).

Yet another object of the invention is to device a low cost visible sensor for the volume of water passed through the cartridge so as to detect the lifetime of the water purifier.

Yet another object of the present invention is to provide a water purification device with a water flow meter having a silver quantum clusters embedded in OTBN to detect the quantity of water flowing.

Yet another object of the invention is to utilize the changes in color in the absorbed visible light with volume of water passed, as an indicator of lifetime of the water purification device.

Still another object of the invention is to utilize the changes in luminescence in the absorbed UV light with volume of water passed, as an indicator of lifetime of the water purification device.

In one aspect, the present disclosure provides a method for detecting the quantity of water flow using silver quantum clusters embedded in organic-templated-boehmite-nanoarchitecture (Ag QCs-OTBN). The OTBN matrix is used for protecting the silver quantum clusters. The method involves monitoring the color of the silver quantum clusters in a light. The change in color of the silver quantum clusters from a first color to a second color indicates a specific amount of contaminated water has been passed.

In another aspect of the present disclosure a water flow meter have been provided. The water flow meter includes a water inlet and a water outlet for flow of water in and out of the flow meter respectively, a sensor and a transparent casing. The sensor is present inside the flow meter. The sensor having silver quantum clusters embedded in organic-templated-boehmite nanoarchitecture (OTBN). The embedding of silver quantum clusters in OTBN protects silver quantum clusters from segregation of ions present in the contaminated water. The transparent casing allows monitoring the color of the sensor when the water is flowing. The change in color of the sensor from a first color to a second color indicates a specific amount of contaminated water have been passed through the water flow meter.

BRIEF DESCRIPTION OF FIGURES

The accompanying figures, which are incorporated in and constitute a part of this specification, illustrate several aspects and together with the description serve to explain the principles of the invention.

DESCRIPTION

The present invention can be understood more readily by reference to the following detailed description of the invention and the examples included therein.

Before the present compounds, compositions, articles, systems, devices, and/or methods are disclosed and described, it is to be understood that they are not limited to specific synthetic methods unless otherwise specified, or to particular reagents unless otherwise specified, as such can, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

All publications mentioned herein are incorporated herein by reference to disclose and describe the methods and/or materials in connection with which the publications are cited.

The novelty of the composition reported here is in the aspect of embedding the silver clusters in a nanoarchitecture matrix which enables protection of silver surface from various ions present in synthetic challenge water.

The present invention discloses the synthesis, characterization and application of silver quantum clusters impregnated organic-templated-boehmite-nanoarchitecture (Ag QCs-OTBN). The as-synthesized Ag QCs-OTBN composition is characterized by a number of spectroscopic and microscopic techniques. The utility of Ag QCs-OTBN as a visible sensor of quantity of water passed through a water purification device has been demonstrated.

The synthesized Ag QCs-OTBN is normally used in a water purification device. More specifically the Ag QCs-OTBN is used in the water flow meters to detect the quantity of water flowing.

Figure 1:
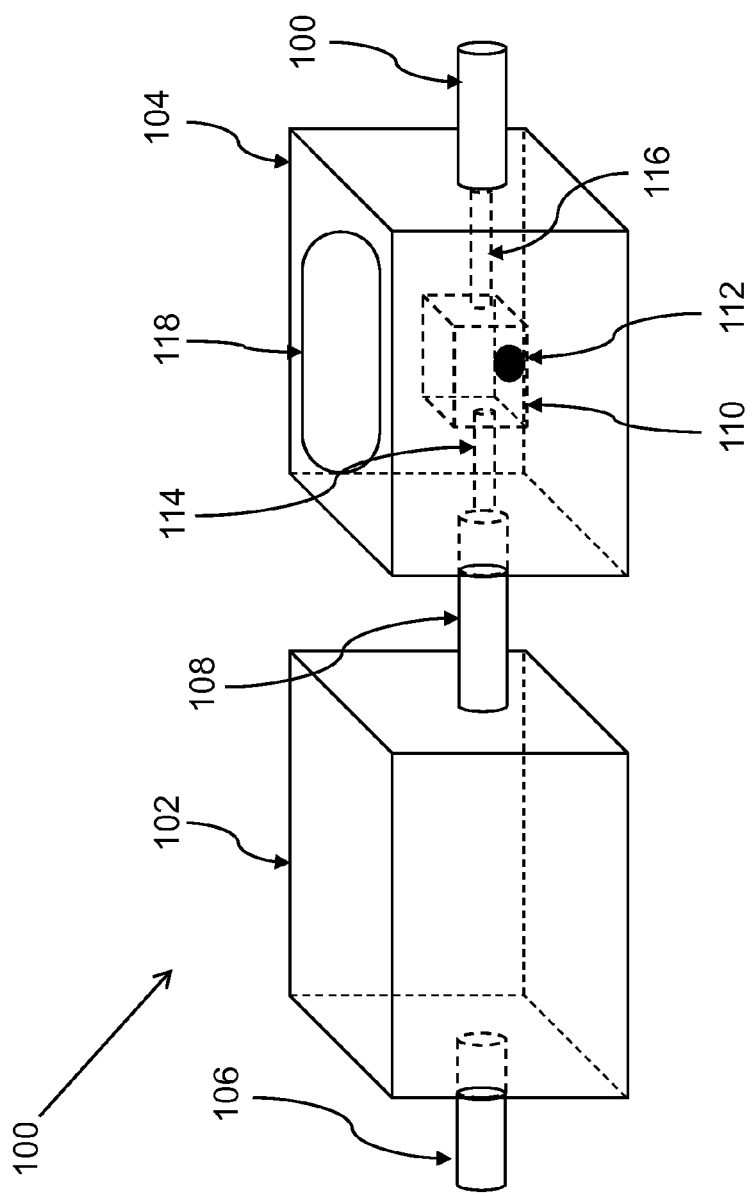
FIG. 1 shows a perspective view a water purification device, in accordance with an aspect of the present invention.

A perspective view of a gravity fed water purification device 100 according to an embodiment of the disclosure is shown in FIG. 1. The various elements shown in FIG. 1 are for the representational purpose. It should be appreciated that the dimensions and design of the gravity fed water purification device 100 and their elements varies as per the requirements. The gravity fed water purification device 100 mainly includes a particulate filter 102 and a water flow meter 104. The gravity fed water purification device 100 is configured to purify the contaminated water.

In an embodiment of the disclosure, the water flow meter 104 is present after the water filter 102 as shown in FIG. 1. In another embodiment of the disclosure, the water flow meter is present before the water filter (not shown in the Fig.). It should be appreciated that the water flow meter 104 can also be used irrespective of the presence of the water filter 104. The use of water flow meter 104 is not limited to the particulate water filter 102. The use of any other type of water filter available in the market is well within the scope of this disclosure.

The contaminated water is provided to the particulate filter 102 through a first inlet 106. The contaminated water is filtered in the particulate filter 102 and passed on to the water flow meter 104 through a first outlet 108. Inside the water flow meter 104, a site 110 has been provided. The site 110 includes a sensor 112. The sensor 112 is silver quantum clusters embedded in the OTBN according to an embodiment of the disclosure. The embedding of silver quantum clusters in OTBN protects silver quantum clusters from segregation of ions present in the water. The water enters the site 110 through a second inlet 114 and goes out of the site 110 from a second outlet 116 as shown in FIG. 1. The water flow meter 104 further includes a transparent casing 118 or a transparent window 118. As the water flows over the silver quantum clusters, the color of silver quantum clusters changes from a first color to a second color. The transparent casing 118 allows a user to monitor the color of the silver quantum clusters embedded in the OTBN. The change in color indicates that a specific amount of water has been passed from the water flow meter and the same amount of water has been purified using the water purification device 100.

Figure 4:
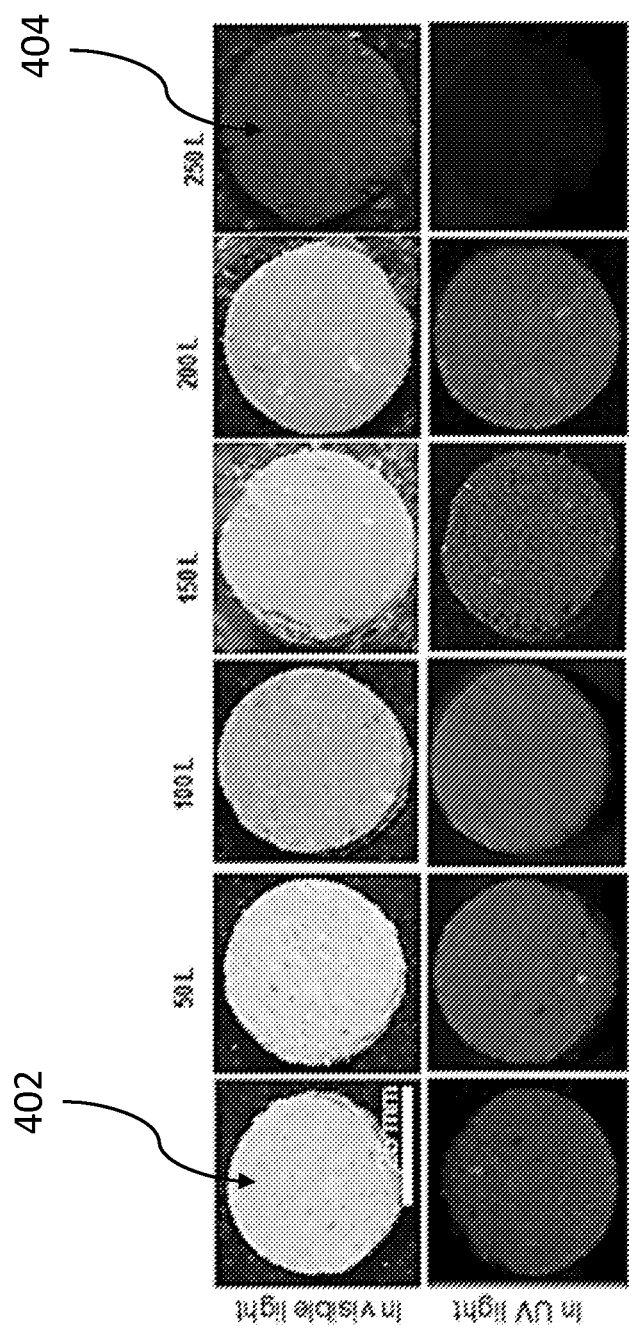
FIG. 4 shows color change observed during the passage of synthetic challenge water through Ag QCs embedded in OTBN (first row: photographs of disc in visible light, second row: photographs of disc in UV light). The color change mentioned here in visible light are 0 L: pink, 50 L: light brown, 100 L: dark brown, 150 L: dark yellow, 200 L: yellowish green, 250 L: black. The color change mentioned here in UV light is 0 L: red, 50 L: violet, 100 L: dull violet, 150 L: dark blue, 200 L: blue, 250 L: black. Images are shown in the shades of black and white in accordance with an aspect of the present invention.

The change in the color of the silver quantum clusters is detected by using one of the visible light or the Ultraviolet light. The various changes in the color of the silver quantum clusters in the visible light or the Ultraviolet light are shown in FIG. 4 according to an embodiment of the disclosure.

Figure 2:
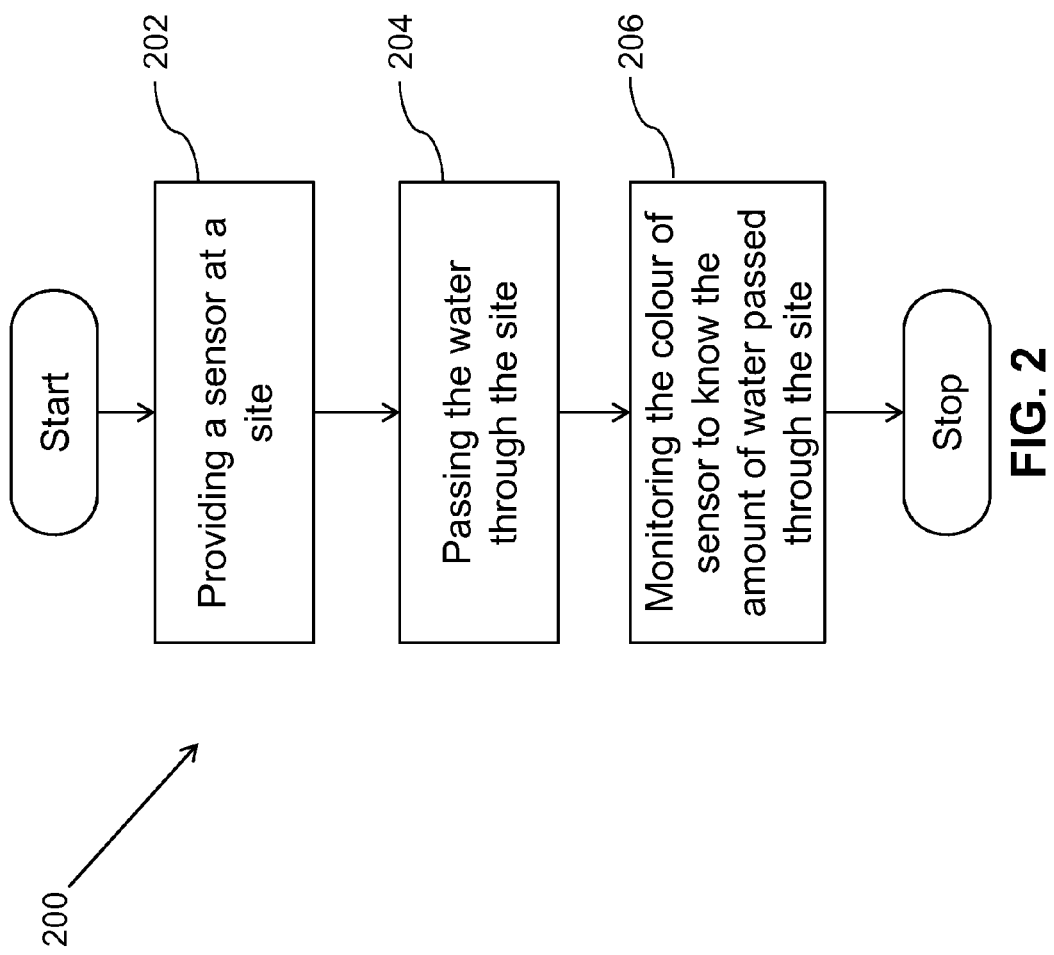
FIG. 2 shows a flowchart showing the method of detecting the quantity of water flow, in accordance with an aspect of the present invention.

A method for detecting the quantity of contaminated water using the water flow meter 104 is shown in a flowchart 200 of FIG. 2 in accordance with the embodiment of FIG. 1. At step 202, the sensor 112 is provided at the site 110. The sensor 112 is silver quantum clusters embedded in the OTBN. The embedding of silver quantum clusters in OTBN protects silver quantum clusters from segregation of ions present in the water. At step 204, the water is passed through the site 112. And finally at step 206, the color of the silver quantum clusters is monitored through the transparent casing 118. The change in color indicates that the specific amount of water has been passed through the water flow meter 104.

The novelty of the composition of silver quantum clusters reported in the disclosure is that the visible sensor based on Ag QCs-OTBN not only assesses the volume of water passed as a mechanical flow meter does; it assesses the lifetime of a cartridge based on the input water quality. A measure of the input water quality can be taken as ionic strength of the input water.

In an embodiment of the disclosure, the output reading of the sensor 112 is calibrated as per the requirement of the user. The sensor 112 is present at a fixed location. When the water flows inside the flow meter 104, then only a certain volume V1 of water out of the total volume of water (coming in the flow meter 104) passes through the sensor 112. Thus, the passing of only certain volume V1 results in color change of the Ag QCs-OTBN sensors from pink to black. For example, say the sensor is placed in such a way that only 10% of water coming in the flow meter 104 passes through the sensor 112. It is noted that the color of sensor 112 has been changed after a passage of 250 L. Since only 10% is flowing through the sensor, so we calculate that a total of 2500 L has passed through the flow meter 104. Therefore, it is necessary to calibrate the output reading of the sensor 112.

In an illustrative embodiment, the present invention describes that the visible color change of the Ag QCs-OTBN from pink to black does not happen after a defined volume of any input water is passed. The color change happens in a reduced volume of water if TDS of the input water is greater than 1,000 ppm and will happen after much larger volume of water, if TDS of the input water is less than 100 ppm.

The efficiency of adsorption based removal of contaminants depends on ionic composition of input water. The interfering ions in the water are known to reduce the capacity/lifetime of the adsorption based filters. Therefore lifetime of the filter will be drastically reduced from the expected capacity if high ionic strength input water is passed. Hence, for any adsorption based filter, it is very important to have a lifetime sensor which works based on input water quality. The following experimental methods and their results describe such a color changing sensor in detail.

EXPERIMENTAL METHODS

Material Characterization

The identification of the phase(s) of the as-prepared sample was carried out by X-ray powder diffraction (Bruker AXS, D8 Discover, USA) using Cu—Kα radiation at λ=1.5418 Å. Surface morphology, elemental analysis and elemental mapping studies were done using a Scanning Electron Microscope (SEM) equipped with Energy Dispersive Analysis of X-rays (EDAX) (FEI Quanta 200). For this, sample in the gel form was re-suspended in water by sonication for 10 min and drop casted on an indium tin oxide (ITO) conducting glass and dried. High Resolution Transmission Electron Microscopy (HRTEM) was done using JEM 3010 (JEOL, Japan). The samples were spotted on amorphous carbon coated copper grids and dried at room temperature. FT-IR spectra were measured using Perkin Elmer Spectrum One instrument and KBr crystals were used as the matrix for preparing samples. Luminescence measurements were carried out by using Jobin Vyon NanoLog instrument. The band pass for excitation and emission was set as 2 nm.

The accompanying examples and figures and examples, which are incorporated in and constitute a part of this specification, illustrate several aspects and together with the description serve to explain the principles of the invention. This should, however, not be construed as limiting the scope of the invention.

Example 1

This example describes the in-situ preparation of silver quantum clusters protected by glutathione in the OTBN gel. OTBN was prepared as reported in the previous patent application (1529/CHE/2010, subsequently also published in the corresponding PCT publication WO 2011/151725 A2). The filtered OTBN gel was used as a matrix for in-situ preparation of silver quantum clusters. The prepared OTBN gel was re-suspended in water, to which silver precursor (silver nitrate, silver fluoride, silver acetate, silver permanganate, silver sulfate, silver nitrite, silver salicylate or a combination thereof) was added drop-wise. The percentage of silver loading in OTBN gel was 3%. After stirring the gel for an hour, surface protecting agent (glutathione) was added drop-wise; then the solution was allowed to stir for an hour. Sodium borohydride was added drop-wise to the above solution at ice-cold condition (molar ratio of silver precursor to reducing agent ratio was 1:4). Then the solution was allowed to stir for an hour, filtered and dried at room temperature (28° C.).

Alumina and aluminum based oxides and oxyhydroxides are key materials in many industrial applications, including catalysis and molecular adsorption (S. Tanada, M. Kabayama, N. Kawasaki, T. Sakiyama, T. Nakamura, M. Araki, T. Tamura, J. Colloid Interface Sci., 2003, 257, 135; H. Y. Zhang, G. B. Shan, H. Z. Liu, J. M. Xing, Chem. Eng. Commun., 2007, 194, 938). Various compounds of aluminum have been prepared for various applications. After realizing the influence of size and shape of the particles on their physical and chemical properties, recent efforts have been mainly directed towards the preparation of various nanostructured alumina and alumina based compounds. As of now, several nanostructured aluminum based compounds with different morphologies, and structures have been prepared. Among the various structures of alumina and aluminum based compounds available, AlOOH and Y-Al2O3 are of special interest in environmental remediation due to their high ion exchange capability and high surface area. So far, material scientists have succeeded in preparing various morphologies of boehmite (AlOOH) and Al2O3, such as nanowires, nanotubes, nanosheets, nanobelts, nanofibers, nanoflowers, nanoflakes, and nanorods by different methods.

According to the literature, the boehmite (AlOOH) phase forms from aluminum hydroxide, Al(OH)$_3$, at about 373 K (Misra, C. Industrial Alumina Chemicals; ACS Monograph 184; American Chemical Society: Washington, D.C., 1986; Chapter 2; Zhu, H. Y., Riches, J. D., Barry, J. C. y-Alumina nanofibers prepared from aluminum hydrate with poly(ethylene oxide) surfactant, Chem. Mater. 2002, 14, 2086-2093). Most of the reported AlOOH nanostructures are synthesized through hydrothermal treatment (temperature: 160-240° C.). However, a simple, quick, energy efficient, eco-friendly, and inexpensive preparation of nanoscale-AlOOH is very important for commercial applications.

The proposed synthetic method is superior to existing methods in various aspects, which has large implications to the chemical industry: (1) synthesis is done at room temperature and at atmospheric pressure (2) enhanced settleability, thereby easy and quick separation of the product (organic templates such as chitosan can act as a flocculating agent), (3) bio-friendly, facile and green synthesis, (4) easy scale-up and, (5) ability to granulate without the aid of any external agents and good physical strength in water, and finally (6) large enhancement in arsenic and fluoride removal performance.

Prior art on the preparation of aluminum based oxides in bead and granular form. Alumina is typically used in the bead form for the removal of fluoride from drinking water. Typically, reported procedure for the bead making is to add binders (organic or inorganic) along with fine particles of alumina/aluminum hydroxide and shape the composite in form of a bead. Thereafter, the bead is heated at elevated temperatures (300-600° C.). In the ceramics industry, particles are agglomerated by spray drying using organic polymers as binders.

Binder-based method: In a typical procedure, appropriate quantity of binder is added to the alumina particles through wet blending. Therefore, the particles are transformed to the shape of a bead through spray drying or granulator or pan coating. The formed beads are firstly dehydrated and thereafter calcined at temperatures above 400° C.

Oil-drop method: In a typical procedure, the gel obtained by precipitation of aluminum precursor using a base is allowed to drop into a hot oil bath, forming spherical particles as partial decomposition of the gelling agent takes place. To complete the coagulation, ageing is then performed at higher pressure and temperature. The final crystalline spherical alumina particles are obtained after washing, drying and calcining at high temperature.

It is clear that aluminum based compounds in general and alumina in particular are the most widely used and they are the basis of demonstrated technology for removing arsenic and fluoride from drinking water. However, the fluoride adsorption capacity of alumina is reported to be in the range of 1-10 mg/g, (Ghorai, S and Pant, K. K., Equilibrium, kinetics and breakthrough studies for adsorption of fluoride on activated alumina, Sep. Purif Technol., 2005, 42(3), 265-271). The maximum arsenic adsorption capacity reported for conventional AA is around 16 mg/g (Kim, Y., Kim, C., Choi, I., Rengaraj, S., Yi, J., Arsenic removal using mesoporous alumina prepared via a templating Method, Environ. Sci. Technol. 2004, 38, 924-931). The low arsenic and fluoride uptake capacity of conventional AA demands frequent regeneration and produces large amount of solid and liquid waste. The other reported problem of commercially available activated alumina is its poor kinetics, which demands large reactor volume to attain the required performance. It is now realized that size, structure and shape play important roles in chemical and physical properties of the material and smaller the crystallite size, better is the performance. However, using nanoparticles as filter medium is impractical due to difficulty in particle separation, danger of particle leaching, and poor hydraulic conductivity. Hence, it has to be granulated like any other powdered material to use as a medium for filtration. The reported methods of alumina granulation are mostly based on addition of binding agents and subsequent calcinations. Such approaches are less environmental friendly and uneconomical. In this application, we have demonstrated an easy, economical, and environment friendly method to make a granular, bio-friendly hybrid material. The material consists of a biopolymer such as chitosan and a nanoscale metal oxyhydroxide (γ-AlOOH), with large adsorption capacity to remove various anions and pathogens from water.

We present the synthesis, characterization and water purification applications of a granulated hybrid material constructed through organic template assisted low temperature (<60° C.) sol-gel process. The process of synthesis was conducted in water medium.

In an exemplary aspect, the low temperature synthesis of nanoscale-AlOOH through a simple soft chemistry route can be performed. The synthesis procedure consists of mixing the aluminum precursor solution with chitosan (dissolved in 1-5% glacial acetic acid or HCl or combination thereof) with vigorous stirring. In a general procedure, a solution of aluminum precursor such as aluminum nitrate was added slowly into the chitosan solution with vigorous stirring for 60 minutes and was kept overnight without agitation. Aqueous ammonia or NaOH solution was slowly added into the metal-chitosan solution with vigorous stirring to facilitate the precipitation of the metal-chitosan composites (pH 7-8.0). All these steps were carried out at temperature below 30° C. Stirring was continued for two hours. The precipitate was filtered, washed to remove any unwanted impurities, converted in the shape of beads and dried at various conditions.

In another exemplary aspect, a similar method has been used to precipitate the metal chitosan composites above 30° C. and below 60° C. The reaction products were filtered, washed to remove any unwanted impurities, converted in the shape of beads and dried at various conditions.

In another exemplary aspect, the materials described above were dried using different drying protocols, including surface drying at room temperature (<35° C.), sun drying (40 to 60° C.) and oven drying (60 to 130° C.) were adopted separately to get stable and hard granular materials. It was found that the hardness of the material largely depends upon the drying methodology and it varies with initial metal precursors. The dried product was stored for further use. Various precursors such as aluminium nitrate, aluminium sulphate, aluminium chloride, aluminium isopropoxide, etc. were tried to study their influence on the composite formation.

Example 2

The method described in example 1 was modified to prepare the glutathione protected fluorescent silver quantum clusters in the OTBN gel material. Silver to glutathione ratio was varied from 1:1 to 1:10.

Example 3

The method described in example 1 was modified to prepare the glutathione protected fluorescent silver quantum clusters on OTBN gel material with various molar ratios of silver to sodium borohydride such as 1:4 and 1:8.

Example 4

The method described in example 1 was modified to prepare clusters with different surface protecting agents like mercaptosuccinic acid, polyvinyl pyrrolidone and trisodium citrate in OTBN gel.

Example 5

This example describes the in-situ preparation of silver quantum clusters protected with glutathione on the OTBN powder. The dried OTBN powder was crushed to a particle size of 100-150 μm. The powder was shaken in water using a shaker to which silver precursor (silver nitrate, silver fluoride, silver acetate, silver permanganate, silver sulfate, silver nitrite, silver salicylate or a combination thereof) was added drop-wise. The percentage of silver loading in OTBN powder was 3%. After shaking the dispersion for an hour, glutathione was added drop wise; then the dispersion was shaken for an hour. Sodium borohydride was added drop-wise to the above dispersion at ice-cold condition (molar ratio of silver to reducing agent ratio was 1:4). Then the dispersion was shaken for an hour, filtered and dried at room temperature (28° C.).

Example 6

This example describes the preparation of silver quantum clusters in a variety of chitosan-metal oxide/hydroxide/oxyhydroxide composite gels. The metal oxide/hydroxide/oxyhydroxide can be based on aluminum, iron, titanium, manganese, cobalt, nickel, copper, silver, zinc, lanthanum, cerium, zirconium or a combination thereof. The synthetic procedure for such a composition is as follows: the chosen salt solution was added slowly into the chitosan solution (dissolved in 1-5% glacial acetic acid or HCl or combination thereof) under vigorous stirring for 60 minutes and kept overnight at rest. Aqueous ammonia or NaOH solution was added slowly into the metal-chitosan solution under vigorous stirring to precipitate the metal-chitosan composites. These gels were used as matrices for the in-situ preparation of ligand protected silver quantum clusters.

Example 7

This example describes the preparation of fluorescent silver quantum clusters on magnetic materials. Superparamagnetic $Fe_3O_4$ was prepared by method as reported in prior art (M. T. Lopez-Lopez, J. D. G. Duran, A. V. Delgado, F. Gonzalez-Caballero, J. Colloid Interface Sci., 2005, 291, 144-151). Freshly prepared superparamagnetic particles were added to the chitosan solution, allowed to stir for 2 h, precipitated at pH 9 using NaOH or aqueous ammonia and filtered to remove the salt contents. Superparamagnetic composite was re-suspended in water, to which silver precursor (silver nitrate, silver fluoride, silver acetate, silver permanganate, silver sulfate, silver nitrite, silver salicylate or a combination thereof) was added drop-wise. The percentage of silver loading in $Fe_3O_4$-chitosan gel was 3%. After stirring the solution for an hour, surface protecting agent (glutathione) was added drop wise; then the solution was allowed to stir for an hour. Sodium borohydride was added drop-wise to the above gel at ice-cold condition (molar ratio of silver to reducing agent ratio was 1:4). Then the solution was allowed to stir for an hour, filtered and dried at room temperature (28° C.).

Example 8

This example describes the visible sensor for volume of water passed through a column using silver quantum clusters in organic-templated-boehmite-nanoarchitecture (Ag QCs-OTBN). A known quantity of Ag QCs-OTBN was packed as a disk of diameter anywhere between 35 mm to 55 mm, in a column. Challenge water having ionic concentration as prescribed by US NSF for testing contaminant removal was used in the study. The output water from a standard carbon block was passed through Ag QCs-OTBN disk at 60 to 120 mL/min flow rate. At periodic intervals, color of the disk was photographed and emission spectra of the material were collected. The change in color from pink to black was observed after the passage of 250 L of water. The material was collected, dried and analyzed using various techniques. Experiment was conducted with the carbon block at the output of the AgQCs-OTBN disk as well.

Example 9

This example describes the visible sensor based on fluorescence quenching of Ag QCs-OTBN to quantify volume of water passed through a column. A known quantity of Ag QCs-OTBN was packed in the form of a disk of diameter anywhere between 35 mm to 55 mm. The feed water was passed through this disk at a flow rate of 80 mL/min. At periodic intervals, color of the disk was photographed and emission spectra of the material were collected. The change in color from pink to black was observed after the passage of 250 L of water. The black material was collected, dried and analyzed using XRD and EDAX.

Results

Figure 3:
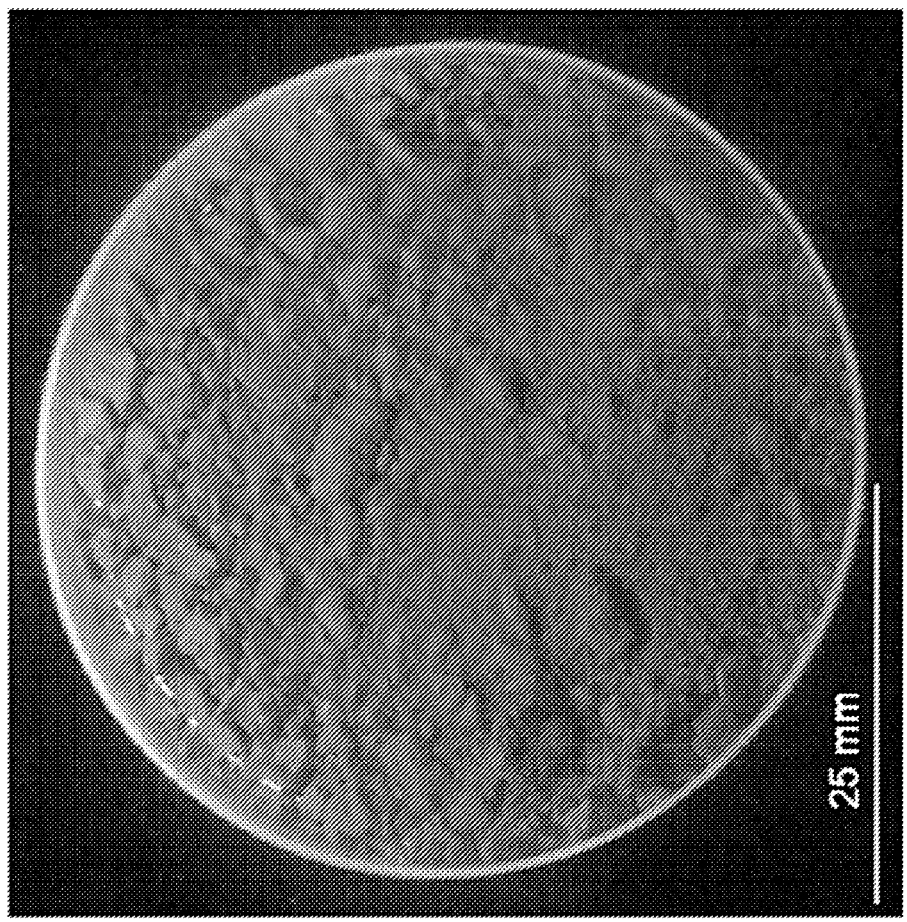
FIG. 3 shows luminescence of glutathione protected Ag QCs embedded in OTBN under UV-lamp (preparation detailed in example 1), in accordance with an aspect of the present invention.

FIG. 3 depicts in gray shades that the Ag QCs-OTBN is highly luminescent under UV light and luminescence can be observed even under low UV intensity (8 W low pressure Hg lamp), in accordance with an aspect of the present invention. The experiments results in the pink luminescence of Ag QCs-OTBN under UV light. 20 g of glutathione-Ag QCs-OTBN, taken in a petri dish and kept under an 8 W low pressure Hg UV lamp. The composition shown here was stable and it exhibited pink luminescence intensity even after a few months of storage under ambient conditions. FIG. 3 displays various shades of black and white as luminescence in the central region of the petri dish. This is in contrast to other monolayer protected Ag clusters reported in the literature as they exhibit poor stability under ambient conditions. The stability of Ag QCs in OTBN is due to the presence of highly protective OTBN environment around the quantum cluster. The role of OTBN matrix in stabilizing nanoparticles has already been demonstrated in our previous patent application (947/CHE/2011). It was shown that the presence of OTBN matrix ensures the stability of silver nanoparticles in synthetic challenge water conditions and can be used successfully for water treatment applications. AgQCs prepared in other matrices as described in Example 6, especially those of titanium, zinc, cerium, and zirconium were also luminescent.

FIG. 4 shows Ag QCs embedded in OTBN is used as a sensor for detecting the volume of water that can be filtered by a water filtration unit, in accordance with an aspect of the present invention. The figure shows the color of the Ag QCs embedded in OTBN changes from brighter shade of gray at 402 to darker shade of gray at 404 after the passage of particular amount of water. As lifetime of any water purifier depends on the input water quality, the Ag QCs-OTBN sensor should indicate the volume of water that can be passed through a filter and also should indicate whether the water purification device is exhausted or not. To achieve this, the output water from the water filtration unit is passed through the sensor material and collected in the storage container. After the passage of water, the color of the Ag QCs-OTBN changes as shown in FIG. 4. First row in FIG. 4 shows color of Ag QCs-OTBN disc in visible light and second row shows luminescence of Ag QCs-OTBN disc in UV light. Prior to the passage of water, the material is pink in color (brighter shade of gray at 402 is shown in FIG. 4) and exhibits high luminescence. Upon passage of water, the material undergoes gradual change and finally turns black (darker shade of gray at 404 is shown in FIG. 4) with quenching in luminescence. The color change mentioned here in visible light are 0 L: pink, 50 L: light brown, 100 L: dark brown, 150 L: dark yellow, 200 L: yellowish green, 250 L: black. The color change mentioned here in UV light is 0 L: red, 50 L: violet, 100 L: dull violet, 150 L: dark blue, 200 L: blue, 250 L: black. Images are shown in the shades of black and white in accordance with an aspect of the present invention. A blank trial with OTBN matrix alone indicated that OTBN matrix does not contribute to the color change upon passage of water. This confirms that the change in color of the material is due to silver quantum clusters. Similar color change was seen in AgQCs prepared in matrices containing titanium, zinc, cerium, and zirconium.

Figure 5:
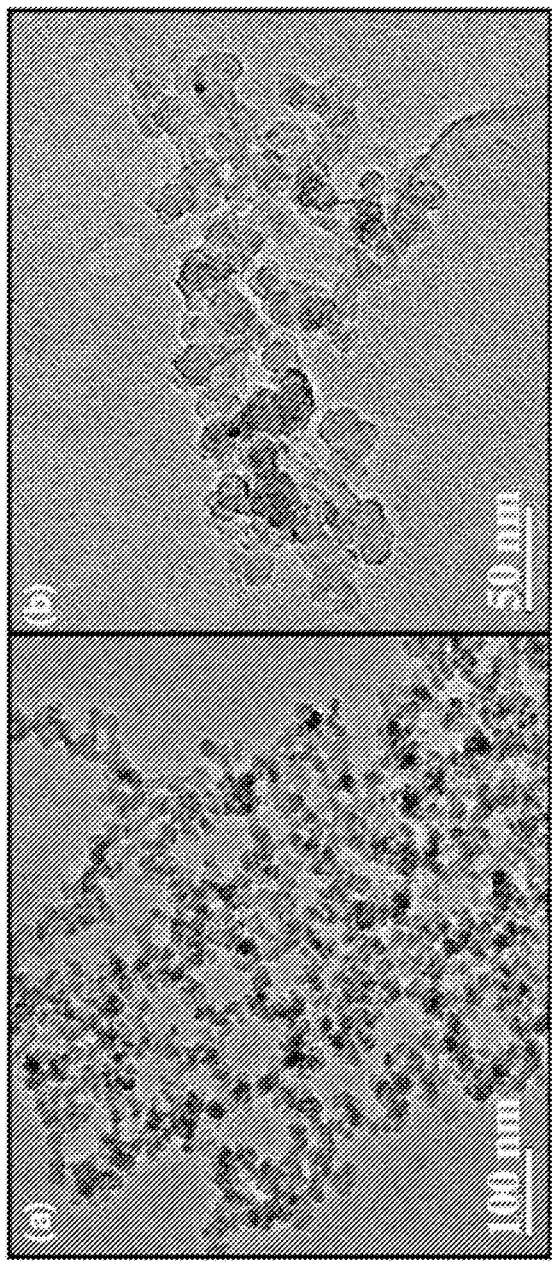
FIG. 5 shows (a) TEM image of Ag QCs embedded in OTBN matrix (b) TEM image of Ag QCs-OTBN, upon electron beam irradiation for 20 minutes, in accordance with an aspect of the present invention.

FIG. 5 (a) shows the TEM image of Ag QCs embedded in OTBN, in accordance with an aspect of the present invention. Clusters in OTBN are not observable in TEM images. This is due to sub-nanometer size of the Ag QC. In the earlier report the formation of large size silver nanoparticles upon electron exposure on naked glutathione protected silver clusters was observed (T. U. B. Rao, B. Nataraju, T. Pradeep, J. Am. Chem. Soc., 2010, 132, 16304-16307). Unlike naked clusters, Ag QCs in OTBN described in this invention was stable under the electron beam (FIG. 5b). The stability of Ag QCs in OTBN under electron beam confirms that Ag cluster is highly protected by the OTBN matrix. Here, the electron beam induced aggregation of silver clusters did not happen as the clusters were embedded inside the OTBN matrix.

Figure 6:
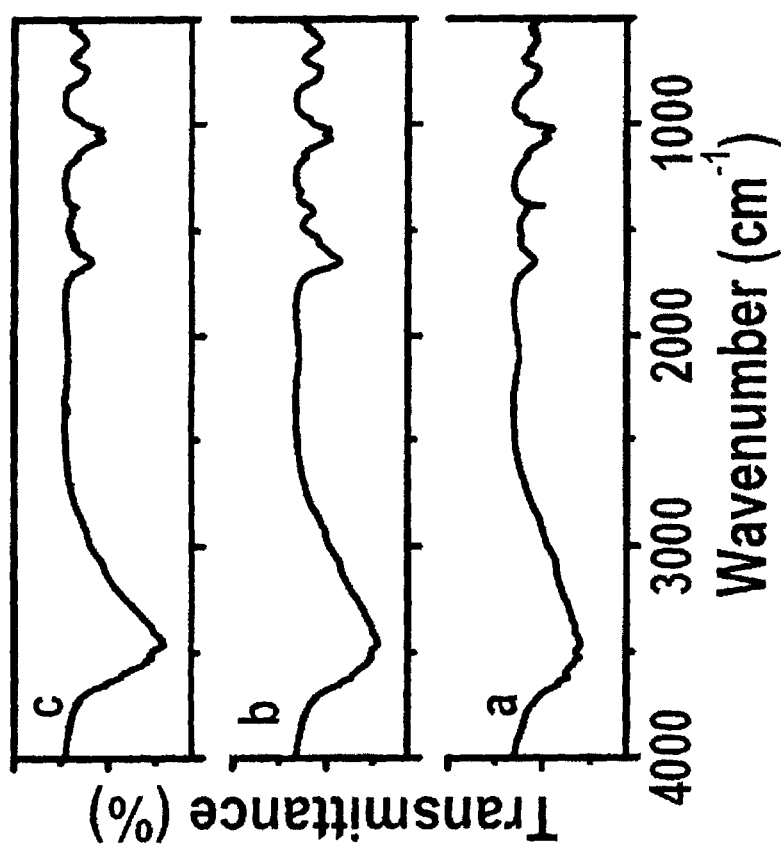
FIG. 6 shows FTIR spectra of (a) OTBN, (b) Ag QCs embedded in OTBN and (c) Ag QCs embedded in OTBN, after passage of 250 L of synthetic challenge water, in accordance with an aspect of the present invention.

FIG. 6 depicts an FTIR spectra of (a) OTBN, (b) Ag QCs embedded in OTBN and (c) Ag QCs embedded in OTBN after passage of 250 L of synthetic challenge water, in accordance with an aspect of the present invention. Impregnation of Ag QCs in OTBN leads to change in the N—H stretching band around 1402 cm$^{-1}$ (shown in curve b). After passage of 250 L synthetic challenge water, N—H band resembles the same as of OTBN. The features present in the region of 2000-500 cm$^{-1}$ confirm the presence of glutathione (M. A. Habeeb Muhammed, S. Ramesh, S. S. Sinha, S. K. Pal and T. Pradeep, Nano Res., 2008, 1, 333-340). The spectra show a strong band at 3450 cm$^{-1}$ due to hydrated water.

Figure 7:
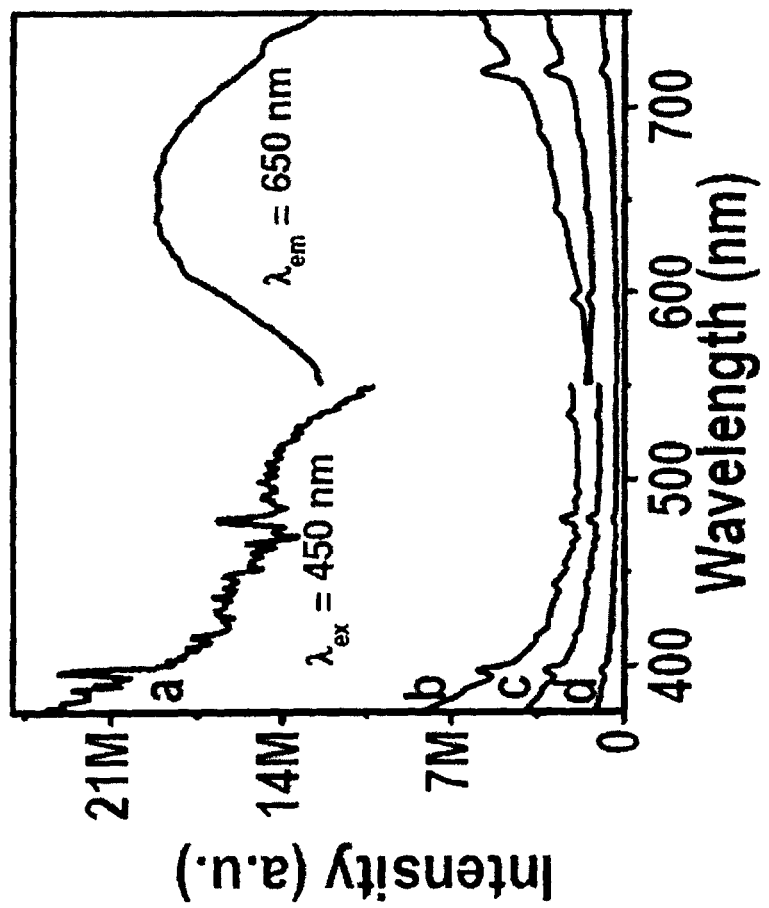
FIG. 7 shows luminescence spectra of (a) Ag QCs embedded in OTBN and those after the passage of (b) 50 L, (c) 150 L and (d) 250 L of water, excited at 450 nm, in accordance with an aspect of the present invention.

FIG. 7 shows a luminescence spectra of (a) Ag QCs embedded in OTBN and those after the passage of (b) 50 L, (c) 150 L and (d) 250 L of water, in accordance with an aspect of the present invention. The excitation spectrum was measured at 450 nm whereas corresponding emission spectrum was measured around 650 nm. It can be observed that the luminescence of Ag QCs-OTBN gradually decreases upon passage of synthetic challenge water. After the passage of 250 L, emission has fully quenched. It is to be noted that peaks observed at λ=400 nm and 475 nm are impurity lines of the excitation source.

Figure 8:
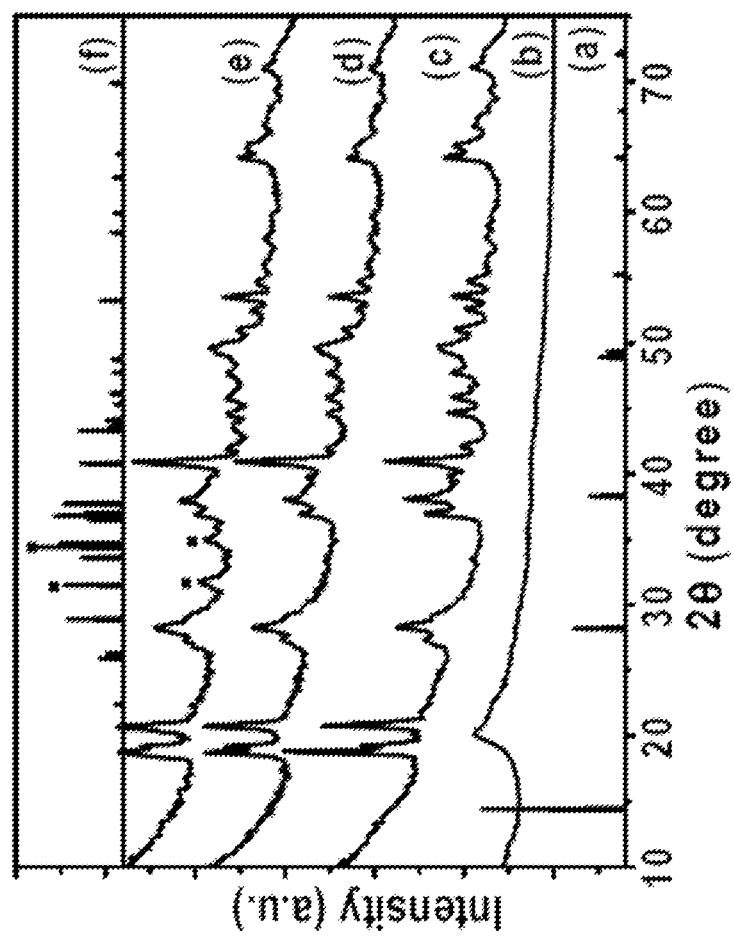
FIG. 8 shows X-ray diffractogram of (a) AlOOH (JCPDS PDF #832384), (b) chitosan, (c) OTBN, (d) silver quantum clusters embedded in OTBN, (e) silver clusters embedded in OTBN after the passage of 250 L of synthetic challenge water and (f) silver sulfide (JCPDS PDF #893840), in accordance with an aspect of the present invention.

FIG. 8 is a X-ray diffractogram of (a) AlOOH (JCPDS PDF #832384), (b) chitosan, (c) OTBN, (d) silver quantum clusters embedded in OTBN, (e) silver clusters embedded in OTBN after the passage of 250 L of synthetic challenge water and (f) JCPDS PDF #893840 of silver sulfide, in accordance with an aspect of the present invention. The peaks attributed to $Ag_2S$ are marked in (e). The XRD of as-synthesized OTBN showed peaks corresponding to (120), (013), (051), (151), (200), (231) and (251) planes (FIG. 8c). All these peaks can be indexed to orthorhombic-AlOOH (JCPDS PDF #832384) (FIG. 8a). The broadened XRD peaks imply that the OTBN crystallite size is very small. The mean crystallite size calculated from the Scherrer formula shows that nanocrystals are of ~3.5 nm. The presence of organic template (chitosan) is also clear from the XRD data. The peaks corresponding to 2θ (in degrees) 18.7°, 20.6°, 41.2° in FIG. 8c are attributed to the presence of the organic template. XRD of Ag QCs-OTBN (FIG. 8d) is not different from OTBN (FIG. 8c). This is due to the fact that clusters are composed of very few atoms and is also smaller than wavelength of X-ray used. FIG. 8e shows that after the passage of 250 liters of water, new peaks appeared corresponding to silver sulfide. The new peaks are indexed based on the pattern of standard silver sulfide (JCPDS PDF #893840) (FIG. 8f). The labeled peaks (marked with (■) are designated as (−121) and (−112) respectively.

Figure 9:
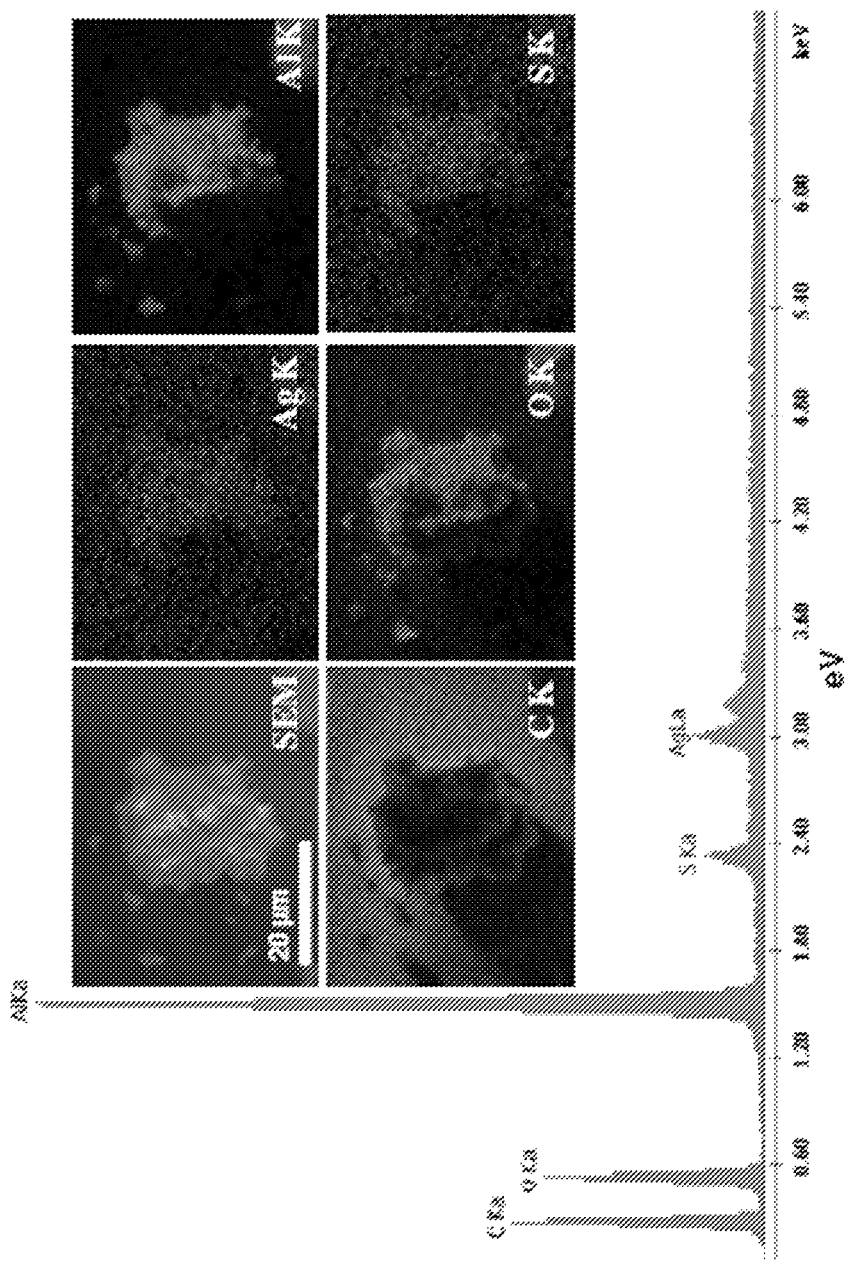
FIG. 9 EDAX spectrum of Ag QCs embedded in OTBN. Inset: elemental X-ray images of Al Kα, O Kα, C Kα, Ag Lα and S Kα of the sample. The corresponding SEM image is also shown in the inset, in accordance with an aspect of the present invention.
Figure 10:
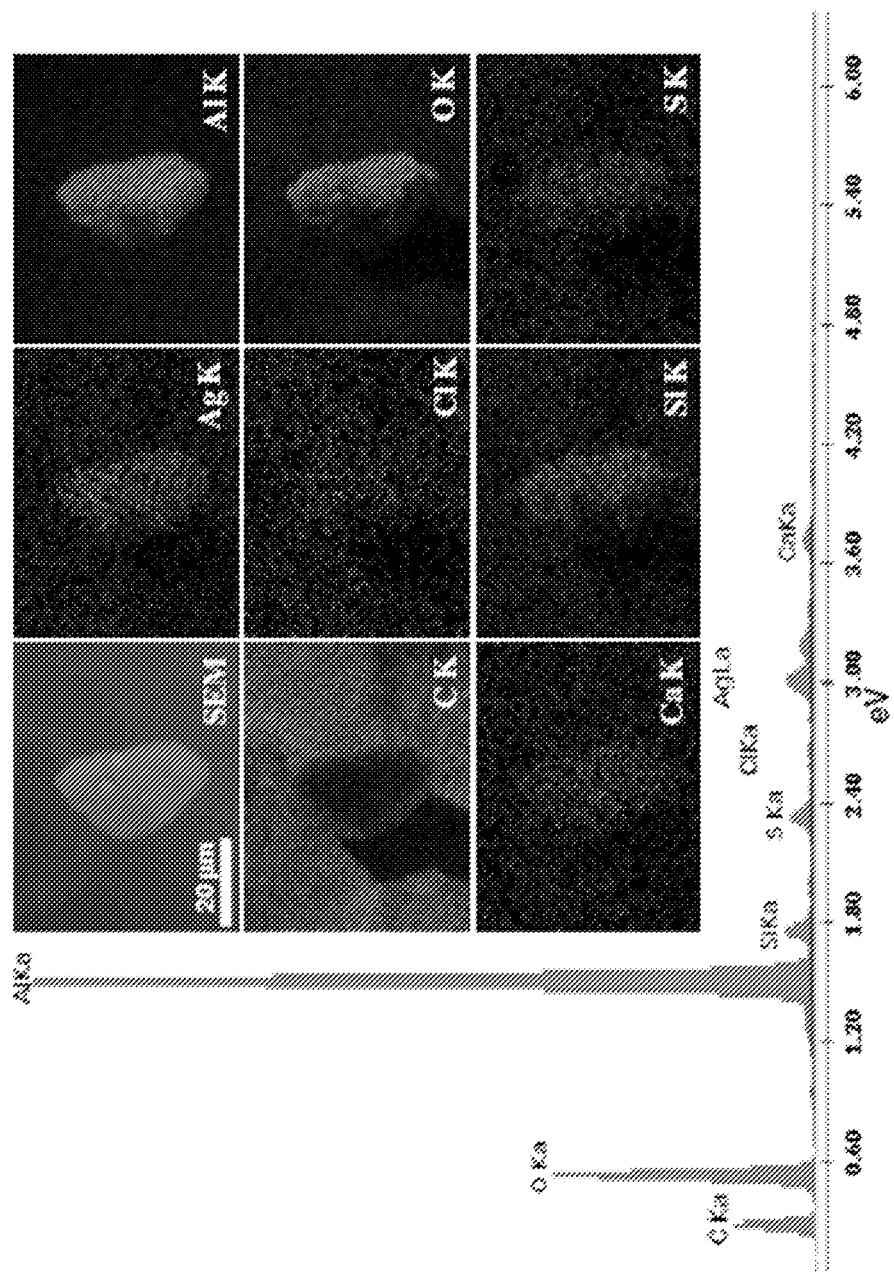
FIG. 10 EDAX spectrum of Ag QCs embedded in OTBN after the passage of 250 L of water. Inset: elemental X-ray images of Al Kα, O Kα, C Kα, Ag Lα, Si Kα, Ca Kα, Cl Kα and S Kα of the sample. The corresponding SEM image is also shown in the inset, in accordance with an aspect of the present invention.

FIG. 9 and FIG. 10 shows EDAX spectrum of as-synthesized QCs embedded in OTBN, in accordance with an aspect of the present invention. This confirms the presence all expected elements such as Ag, S, C and O. The inset shows SEM and its elemental mapping before the passage of water. EDAX spectrum after the passage of 250 L of synthetic challenge water is shown in FIG. 10 and it confirms the presence of all the expected elements such as Al, O K, C K, Ag L, Si K, Ca K, Cl K and S K. Ca, Si and Cl are from water. The inset shows the SEM and elemental maps of the material after the passage of water. The presence of Ca, Si and Cl on Ag QCs-OTBN indicates that the quenching in luminescence and change in color is due to salt induced aggregation of silver quantum clusters. Images in FIG. 9 and FIG. 10 are shown in the shades of black and white in accordance with an aspect of the present invention.

The described aspects are illustrative of the invention and not restrictive. It is therefore obvious that any modifications described in this invention, employing the principles of this invention without departing from its spirit or essential characteristics, still fall within the scope of the invention. Consequently, modifications of design, methods, structure, sequence, materials and the like would be apparent to those skilled in the art, yet still fall within the scope of the invention.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method for detecting the quantity of contaminated water flow, the method comprising: providing a sensor at a site, wherein the sensor having quantum clusters embedded in organic-templated-nanometal oxyhydroxide, the embedding in organic-templated-nanometal oxyhydroxide protects quantum clusters from ions present in the contaminated water; passing contaminated water through the site; and monitoring the color of the sensor in a light, wherein the change in color from a first color to a second color indicating a specific amount of contaminated water have been passed through the site.

2. The method of claim 1, wherein the light is at one of a visible light or an Ultraviolet light.

3. The method of claim 1, wherein the organic-templated-nanometal oxyhydroxide is organic-templated-boehmite nanoarchitecture (OTBN).

4. The method of claim 1, wherein the quantum clusters is silver quantum clusters.

5. The method of claim 4, wherein the silver quantum clusters are embedded in OTBN by impregnating a plurality of silver ions with OTBN in the gel state, wherein the silver ions reduced to a zero valent state by the use of a reducing agent and protecting by a surface protecting agent.

6. The method of claim 4, wherein silver quantum clusters are embedded in OTBN by contacting externally prepared silver quantum clusters with OTBN in the gel state.

7. The method of claim 4, wherein silver quantum clusters are embedded in OTBN by contacting externally prepared silver quantum clusters with OTBN in the solid state.

8. The method of claim 4 further includes the process of drop-wise addition of one of silver ion or silver quantum clusters to OTBN.

9. The method of claim 4 further includes soaking of silver quantum clusters in OTBN for duration of about 30 minutes to about 12 hours.

10. The method of claim 1, wherein the organic template is prepared of at least one of a chitosan, a banana silk and cellulose.

11. The method of claim 5, wherein the reducing agent is sodium borohydride.

12. The method of claim 1 further includes a silver precursor used for the preparation of silver quantum clusters, wherein the silver precursor is a made of at least one of a silver nitrate, silver fluoride, silver acetate, silver sulfate and silver nitrite.

13. The method of claim 1, wherein the weight ratio of silver quantum cluster to OTBN is about 0.01% to about 10%.

14. The method of claim 1, wherein the weight ratio of silver quantum cluster to OTBN is about 0.01% to about 5%.

15. The method of claim 5, wherein the concentration of the reducing agent is ranging from about 0.005 M to about 1 M.

16. The method of claim 1 wherein quantum clusters is based on at least one of a silver, gold, copper, iron, nickel, platinum and palladium.

17. The method of claim 1 wherein the nanometal is at least one of an aluminium, iron, titanium, manganese, cobalt, nickel, copper, silver, zinc, lanthanum, cerium and zirconium.

18. A gravity fed water purification device comprising: a particulate filter configured to filter the water; a first inlet allowing water to move in the particulate filter; a first outlet configured to pass the water out of the particulate filter; and a water flow meter configured to receive the water from the particulate filter, wherein the water flow meter comprising: a sensor present inside the flow meter, wherein the sensor having silver quantum clusters embedded in organic-templated-boehmite nanoarchitecture (OTBN), the embedding of silver quantum clusters in OTBN protects silver quantum clusters from segregation of ions present in the water; and a transparent casing allows monitoring the change of color of the sensor when the water is flowing, wherein the change in color from a first color to a second color indicating a specific amount of contaminated water have been passed through the water flow meter.

19. A water flow meter comprising: a second inlet for flowing of water inside the flow meter; a second outlet for flowing of water outside the flow meter; a sensor present inside the flow meter, wherein the sensor having silver quantum clusters embedded in organic-templated-boehmite nanoarchitecture (OTBN), the embedding of silver quantum clusters in OTBN protects silver quantum clusters from segregation of ions present in the contaminated water; and a transparent casing allows monitoring the color of the sensor when the water is flowing, wherein the change in color from a first color to a second color indicating a specific amount of contaminated water have been passed through the water flow meter.

20. The water flow meter of claim 19, wherein the OTBN is in the form of a plurality of granules.

21. The water flow meter of claim 19, wherein the particle size of the plurality of granules is from about 0.3 mm to about 5 mm.

22. The water flow meter of claim 19, wherein the particle size of the plurality of granules is from about 0.3 mm to about 1 mm.

* * * * *